United States Patent
Davison et al.

(10) Patent No.: US 11,413,087 B2
(45) Date of Patent: Aug. 16, 2022

(54) END EFFECTOR FOR ELECTROSURGICAL INSTRUMENT WITH IRRIGATION

(71) Applicant: ETHICON LLC, Guaynabo, PR (US)

(72) Inventors: Mark A. Davison, Mainville, OH (US); Mark E. Tebbe, Lebanon, OH (US); Kristen G. Denzinger, Cincinnati, OH (US); Ryan M. Asher, Cincinnati, OH (US); Craig T. Davis, Cincinnati, OH (US); Kevin Bash, Cincinnati, OH (US); Eric Roberson, Cincinnati, OH (US); John E. Brady, Liberty Township, OH (US); Jeffrey A. Bullock, Cincinnati, OH (US); Jeffrey L. Aldridge, Lebanon, OH (US); Monica L. Zeckel, Zionsville, IN (US); Shan Wan, Mason, OH (US); Kristen L. D'Uva, Cincinnati, OH (US)

(73) Assignee: Cilag GmbH International, Zug (CH)

( * ) Notice: Subject to any disclaimer, the term of this patent is extended or adjusted under 35 U.S.C. 154(b) by 1045 days.

(21) Appl. No.: 15/692,342

(22) Filed: Aug. 31, 2017

(65) Prior Publication Data
US 2019/0059988 A1 Feb. 28, 2019

(51) Int. Cl.
*A61B 18/14* (2006.01)
*A61B 18/00* (2006.01)
*A61B 18/12* (2006.01)

(52) U.S. Cl.
CPC ...... *A61B 18/1445* (2013.01); *A61B 18/1402* (2013.01); *A61B 2018/00005* (2013.01); *A61B 2018/00035* (2013.01); *A61B 2018/0063* (2013.01); *A61B 2018/00529* (2013.01); *A61B 2018/00636* (2013.01); *A61B 2018/00916* (2013.01); *A61B 2018/126* (2013.01); *A61B 2018/145* (2013.01); *A61B 2018/1417* (2013.01); *A61B 2018/1467* (2013.01); *A61B 2018/1472* (2013.01); *A61B 2218/002* (2013.01); *A61B 2218/007* (2013.01)

(58) Field of Classification Search
CPC combination set(s) only.
See application file for complete search history.

(56) References Cited

U.S. PATENT DOCUMENTS

| | | | |
|---|---|---|---|
| 5,792,135 A | 8/1998 | Madhani et al. |
| 5,817,084 A | 10/1998 | Jensen |
| 5,878,193 A | 3/1999 | Wang et al. |
| 6,231,565 B1 | 5/2001 | Tovey et al. |

(Continued)

OTHER PUBLICATIONS

U.S. Appl. No. 15/247,559, filed Sep. 23, 2016.
(Continued)

*Primary Examiner* — Joseph A Stoklosa
*Assistant Examiner* — Adam J Avigan
(74) *Attorney, Agent, or Firm* — Frost Brown Todd LLC

(57) ABSTRACT

An apparatus includes a shaft assembly and an end effector. The shaft assembly includes an outer sheath, at least one irrigation conduit, and at least one suction conduit. The end effector includes a first electrode, a second electrode, and a web. The electrodes extend distally relative to a distal end of the outer sheath. The electrodes are operable to apply bipolar RF energy to tissue. The web extends laterally between the first and second electrodes. The web is positioned distal to the distal end of the outer sheath.

15 Claims, 22 Drawing Sheets

(56) References Cited

U.S. PATENT DOCUMENTS

| | | |
|---|---|---|
| 6,364,888 B1 | 4/2002 | Niemeyer |
| 6,558,385 B1 | 5/2003 | McClurken et al. |
| 6,783,524 B2 | 8/2004 | Anderson |
| 7,524,320 B2 | 4/2009 | Tierney et al. |
| 7,691,098 B2 | 4/2010 | Wallace et al. |
| 7,806,891 B2 | 10/2010 | Nowlin et al. |
| 8,479,969 B2 | 7/2013 | Shelton, IV |
| 8,573,461 B2 | 11/2013 | Shelton, IV et al. |
| 8,573,465 B2 | 11/2013 | Shelton, IV |
| 8,602,288 B2 | 12/2013 | Shelton, IV et al. |
| 8,616,431 B2 | 12/2013 | Timm et al. |
| 8,783,541 B2 | 7/2014 | Shelton, IV et al. |
| 8,800,838 B2 | 8/2014 | Shelton, IV |
| 8,820,605 B2 | 9/2014 | Shelton, IV |
| 8,844,789 B2 | 9/2014 | Shelton, IV et al. |
| 9,301,759 B2 | 4/2016 | Spivey et al. |
| 9,572,622 B2 | 2/2017 | Shelton, IV et al. |
| 9,782,220 B2 | 10/2017 | Mark et al. |
| 9,795,440 B2 | 10/2017 | Mark et al. |
| 2007/0016182 A1* | 1/2007 | Lipson .................. A61B 18/12 606/34 |
| 2007/0270798 A1* | 11/2007 | Lu ...................... A61B 18/1445 606/51 |
| 2010/0168729 A1* | 7/2010 | Wang ................ A61B 18/1492 606/33 |
| 2011/0125146 A1* | 5/2011 | Greeley ................ A61B 18/14 606/33 |
| 2016/0361115 A1 | 12/2016 | Bencini et al. |

OTHER PUBLICATIONS

U.S. Appl. No. 15/434,711, filed Feb. 16, 2017.
International Search Report and Written Opinion dated Jan. 30, 2019 for Application No. PCT/IB2018/056329, 18 pgs.

\* cited by examiner

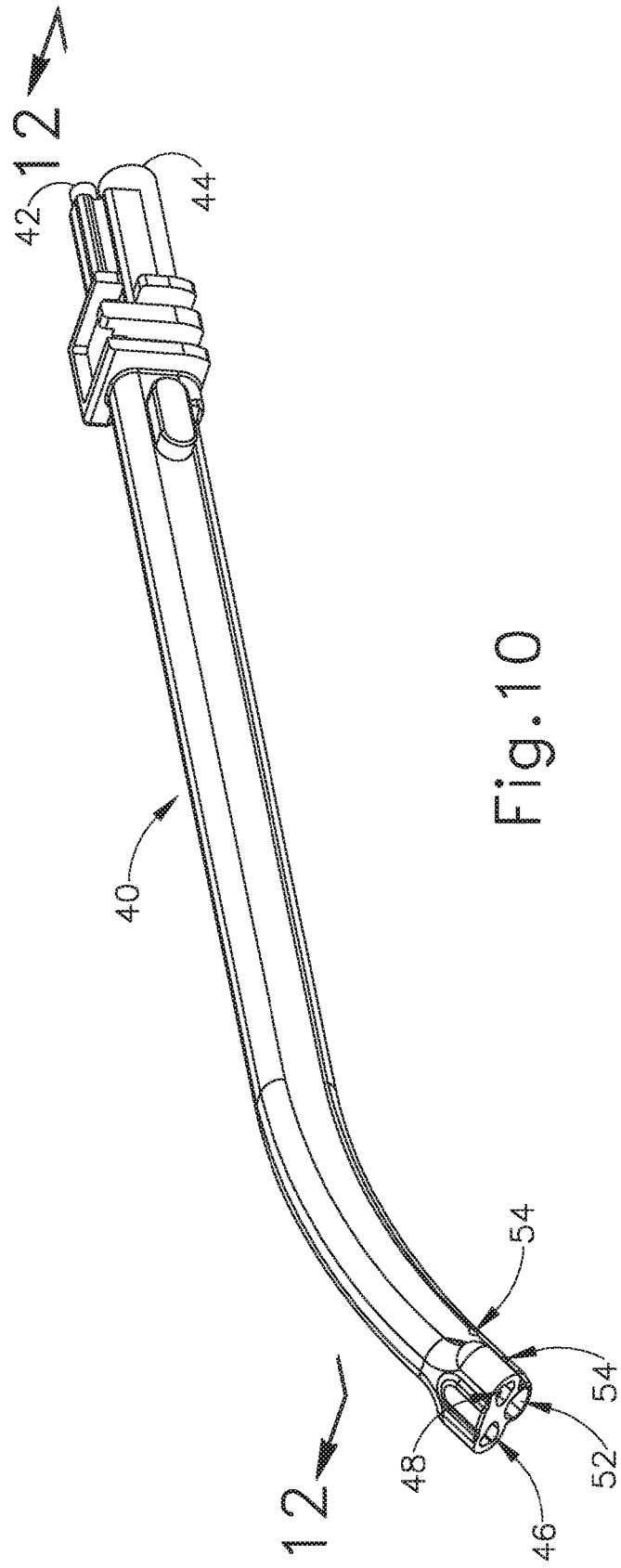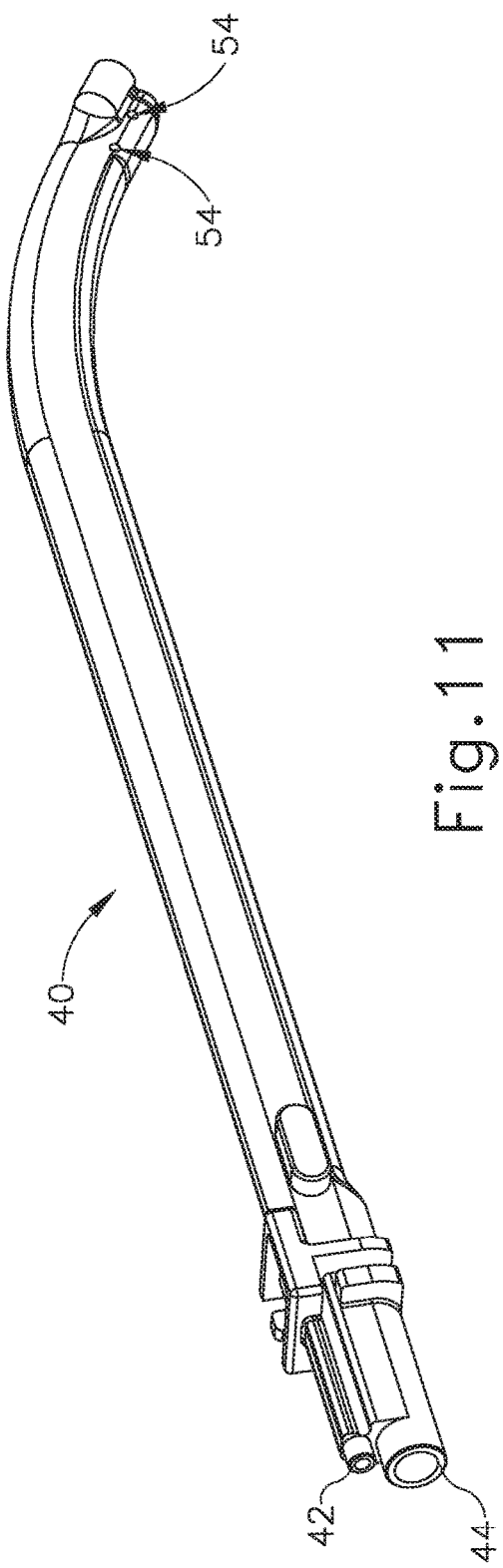
Fig. 10
Fig. 11

END EFFECTOR FOR ELECTROSURGICAL INSTRUMENT WITH IRRIGATION

BACKGROUND

Blood vessels may be transected as a routine aspect of various surgical procedures. This may warrant use of instrumentation to seal or otherwise close off transected blood vessels to stop the bleeding. One merely illustrative example of such a surgical procedure is liver lobectomy. In such a procedure, one surgical instrument (e.g., conventional Kelley clamp, etc.) may be used to crush and thereby fracture the parenchyma tissue of the liver, which may leave fractured parenchyma portions coupled by relatively large blood vessels and/or bile ducts, etc. Those large blood vessels and/or bile ducts, etc. may be transected and sealed using at least one second surgical instrument (e.g., stapler, ultrasonic surgical instrument, RF electrosurgical instrument). Even with such large blood vessels and/or bile ducts sealed, the newly exposed surface of the liver parenchyma may still include relatively small vessels that were transected during the initial act of fracturing the parenchyma tissue. Such transected vessels may continue to bleed; and may be difficult to seal using the same surgical instrument that was used to seal the relatively large blood vessels and/or bile ducts, etc.

Electrosurgical instruments may be used to apply radio frequency (RF) energy to tissue to thereby seal the tissue. Some such instruments include an end effector with at least two electrodes at opposite polarities, such that the end effector is operable to apply bipolar RF energy to tissue. In addition, some such instruments may emit saline or some other fluid at or near the end effector. Such fluid may promote electrical conductivity at the electrode-tissue interface and provide cooling to the electrodes. An example of such an end effector is disclosed in U.S. Pat. No. 9,572,622, entitled "Bipolar Electrosurgical Features for Targeted Hemostasis," issued Feb. 21, 2017, the disclosure of which is incorporated by reference herein. Additional examples of irrigating electrosurgical instruments are disclosed in U.S. patent application Ser. No. 15/274,559, entitled "Electrosurgical Instrument with Fluid Diverter," filed Sep. 23, 2016, issued as U.S. Pat. No. 10,751,117 on Aug. 25, 2020, the disclosure of which is incorporated by reference herein; and U.S. patent application Ser. No. 15/434,711, entitled "Electrosurgical Instrument with Telescoping Suction Port and Debris Cleaner," filed Feb. 16, 2017, issued as U.S. Pat. No. 11,033,325 on Jun. 15, 2021, the disclosure of which is incorporated by reference herein.

It may be desirable to provide an electrosurgical instrument that is readily usable to seal relatively small vessels that are left exposed and bleeding at the newly exposed surface of a fractured liver parenchyma. Such an instrument may also be useful in other clinical contexts and procedures, including but not limited to spinal or orthopedic procedures.

While various types of electrosurgical instruments have been made and used, it is believed that no one prior to the inventor(s) has made or used the invention described herein.

BRIEF DESCRIPTION OF THE DRAWINGS

The accompanying drawings, which are incorporated in and constitute a part of this specification, illustrate embodiments of the invention, and, together with the general description of the invention given above, and the detailed description of the embodiments given below, serve to explain the principles of the present invention.

FIG. 10 depicts a perspective view of a shaft of the instrument of FIG. 1;

FIG. 11 depicts another perspective view of the shaft of FIG. 10;

Figure 1:
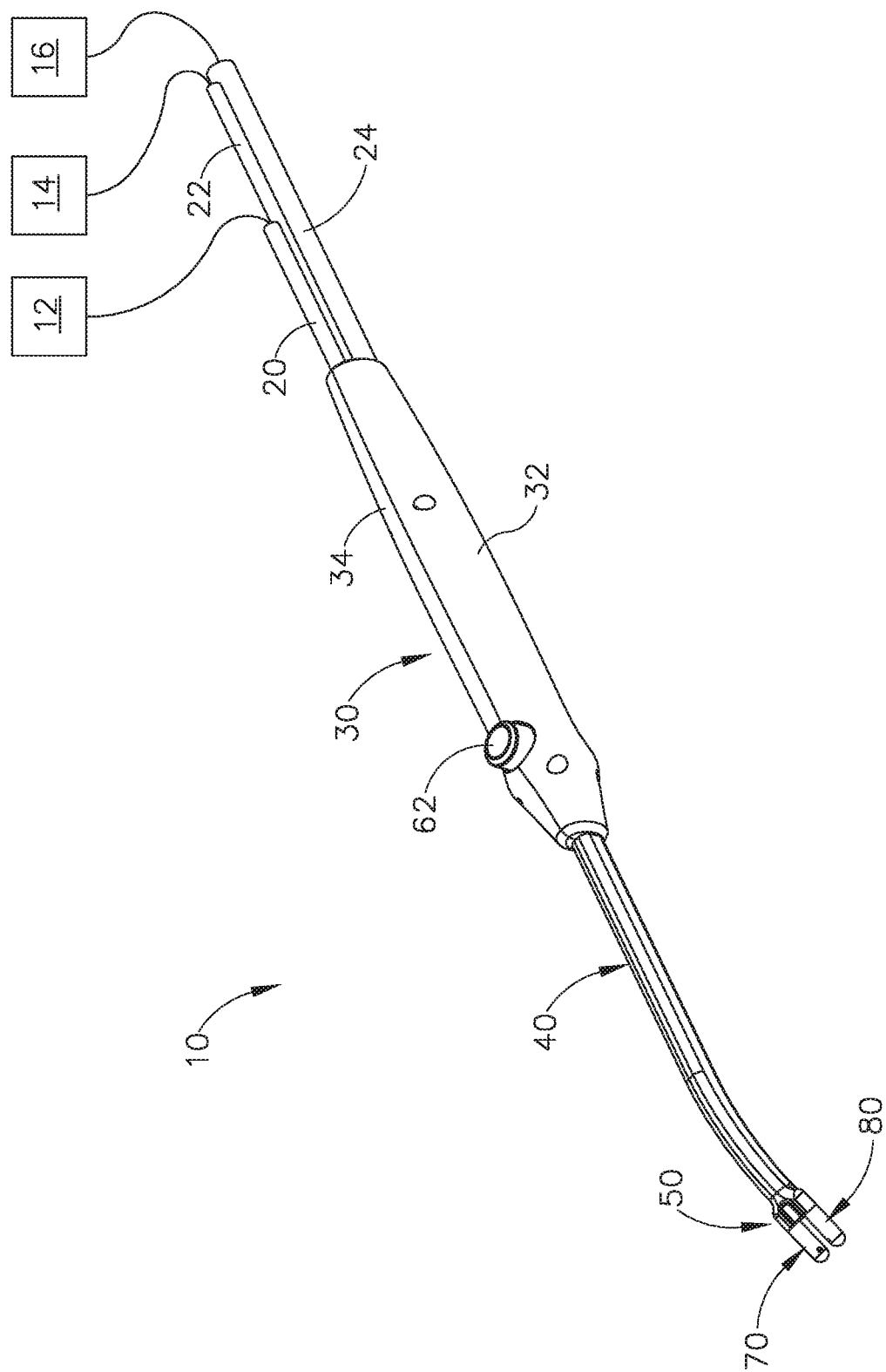
FIG. 1 depicts a perspective view of an exemplary electrosurgical instrument.

The drawings are not intended to be limiting in any way, and it is contemplated that various embodiments of the invention may be carried out in a variety of other ways, including those not necessarily depicted in the drawings. The accompanying drawings incorporated in and forming a part of the specification illustrate several aspects of the present invention, and together with the description serve to explain the principles of the invention; it being understood, however, that this invention is not limited to the precise arrangements shown.

DETAILED DESCRIPTION

The following description of certain examples of the invention should not be used to limit the scope of the present invention. Other examples, features, aspects, embodiments, and advantages of the invention will become apparent to those skilled in the art from the following description, which is by way of illustration, one of the best modes contemplated for carrying out the invention. As will be realized, the invention is capable of other different and obvious aspects, all without departing from the invention. Accordingly, the drawings and descriptions should be regarded as illustrative in nature and not restrictive.

I. Exemplary Electrosurgical Instrument with Saline Irrigation

FIG. 1 shows an exemplary electrosurgical instrument (10) that is operable to apply bipolar RF energy to tissue. By way of example only instrument (10) may be used to seal relatively small vessels (e.g., vessels having a diameter up to approximately 1 mm) that are left exposed and bleeding at the newly exposed surface of a fractured liver parenchyma. In addition, or in the alternative, instrument (10) may be used in various other clinical contexts and procedures as will be apparent to those of ordinary skill in the art in view of the teachings herein, including but not limited to spinal or orthopedic procedures. Instrument (10) of this example comprises a handle assembly (30), a shaft (40), and an end effector (50). Handle assembly (30) is configured to be grasped by a single hand of an operator. End effector (50) includes a pair of electrodes (70, 80) that are operable to contact tissue and thereby apply bipolar RF energy to the tissue.

In the present example, instrument (10) is coupled with a source of electrical power (12) via a flexible cable assembly (20); with a source of saline (14) via a flexible tube (22); and with a source of suction (16) via another flexible tube (24). Cable assembly (20) includes at least two wires (not shown) that extend through shaft (40) to electrodes (70, 80), with at least one wire being coupled with electrode (70) and with at least one other wire being coupled with electrode (80). Electrical power source (12) may comprise any kind of power source that is operable to deliver bipolar RF electrosurgical power to electrodes (70, 80) through the wires of cable assembly (20). Saline source (14) may comprise a conventional saline bag positioned higher than instrument (10), such that instrument (10) receives saline via gravity feed. Alternatively, saline may be actively pumped from a reservoir or be otherwise delivered to instrument (10). Suction source (16) may comprise a conventional vacuum pump or any other suitable kind of device that is operable to generate suction. Tubes (22, 24) may comprise conventional flexible tubing.

Figure 2:
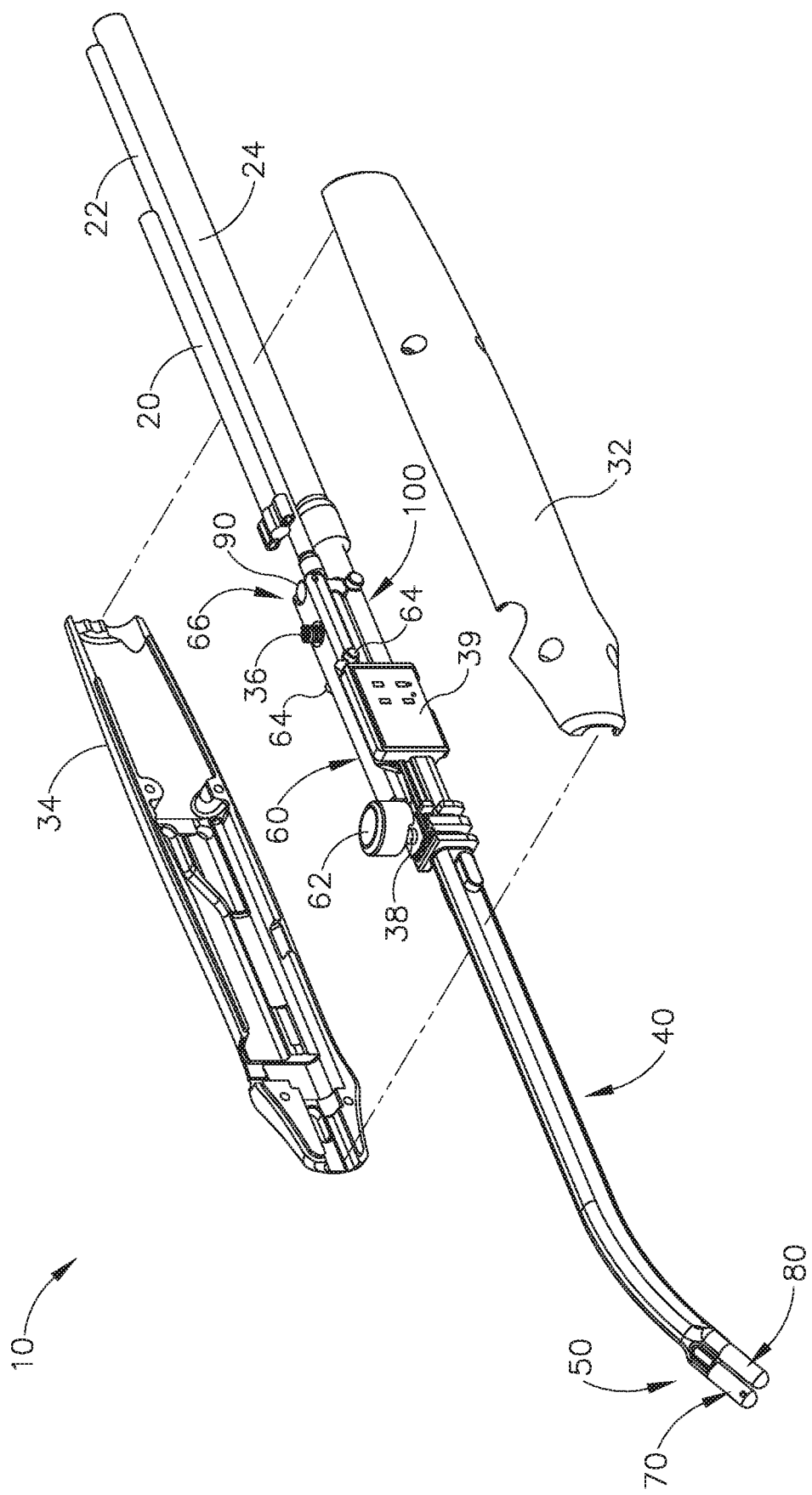
FIG. 2 depicts a partially exploded perspective view of the instrument of FIG. 1.

Handle assembly (30) comprises a first housing (32) and a second housing (34), which couple together to enclose various internal components and provide a handle for grasping by the operator. Cable assembly (20) and tubes (22, 24) extend proximally from handle assembly (30); while shaft (40) extends distally from handle assembly (30). As shown in FIG. 2, an actuator (60), valve body (100), switch (38), and circuit board (39) are contained within handle assembly (30). Switch (38) is coupled with circuit board (39) via wires (not shown); and circuit board (39) is coupled with electrodes (70, 80) via wires. Circuit board (39) is also coupled with wires that are part of cable assembly (20). As will be described in greater detail below, actuator (60) is operable to selectively actuate switch (38) to thereby selectively activate electrodes (70, 80) with RF energy.

Figure 3:
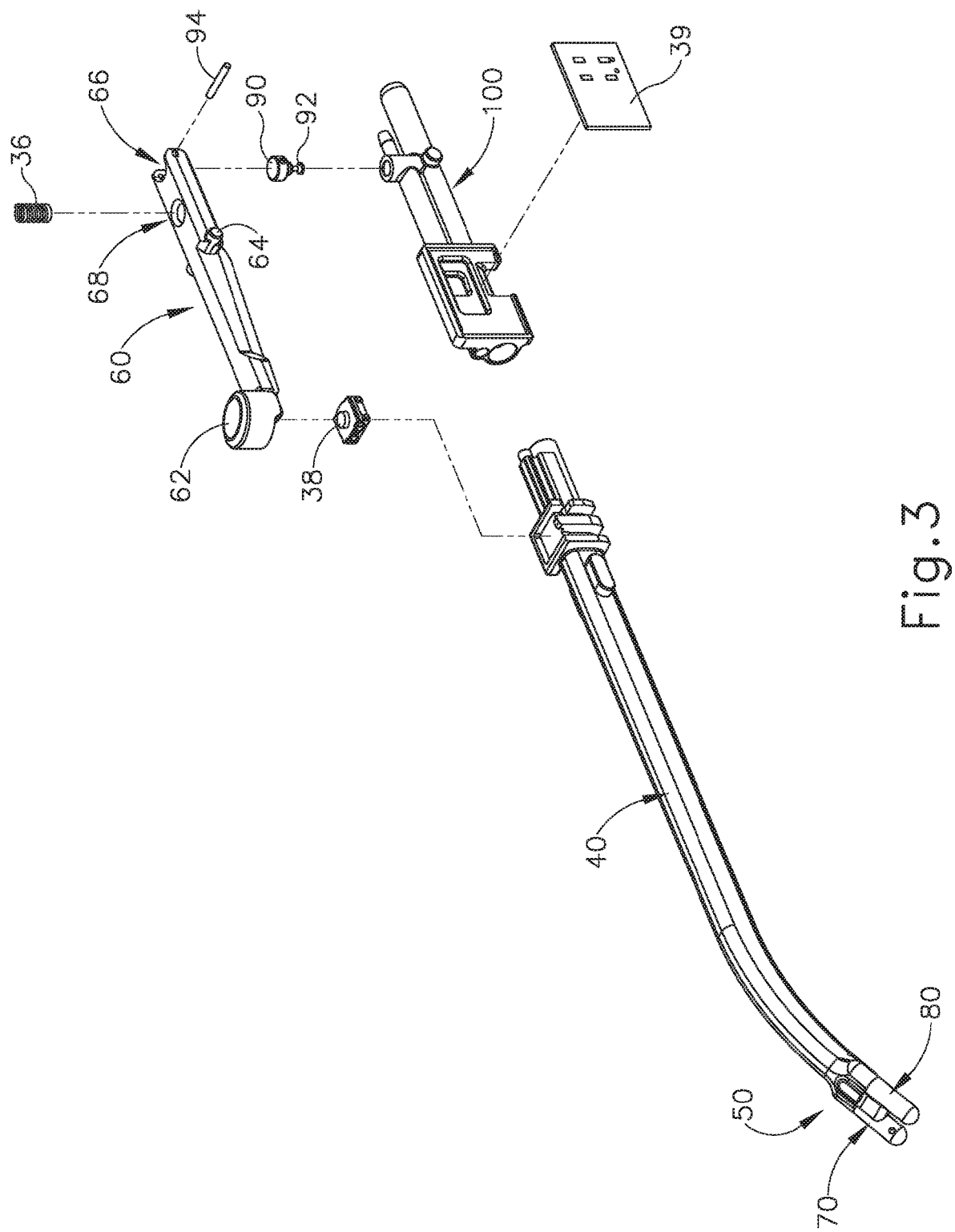
FIG. 3 depicts an exploded perspective view of internal components and shaft components of the instrument of FIG. 1.
Figure 6:
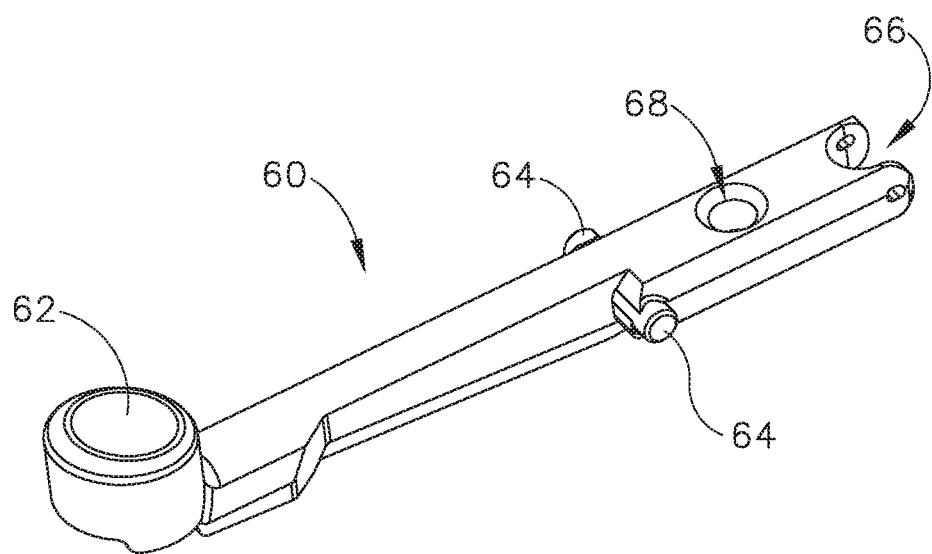
FIG. 6 depicts a perspective view of an actuator of the instrument of FIG. 1.
Figure 7:
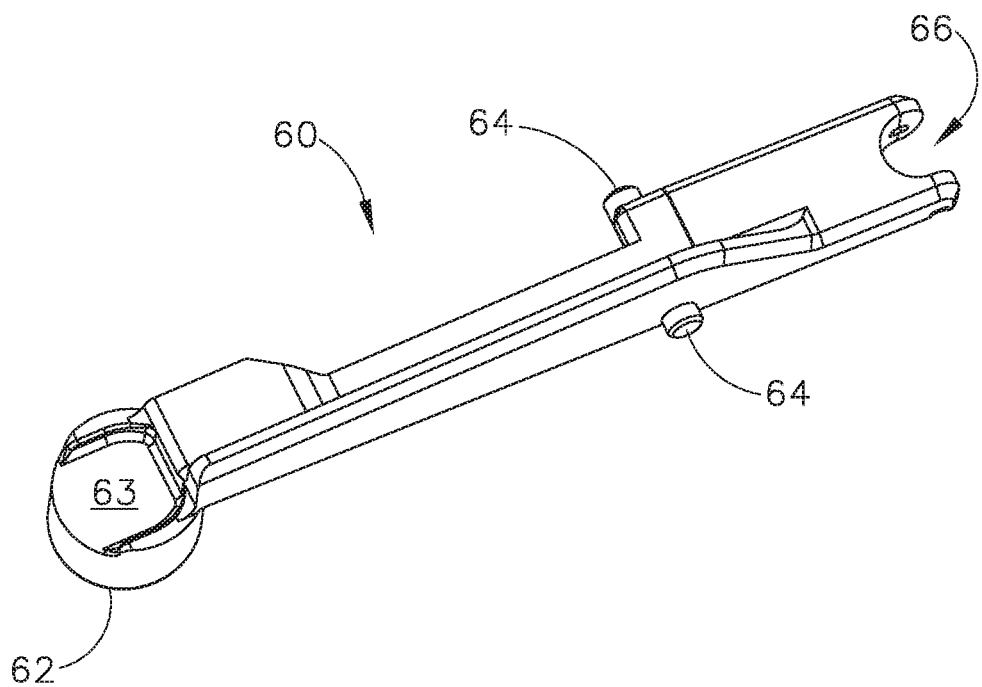
FIG. 7 depicts another perspective view of the actuator of FIG. 6.

As shown in FIG. 3, switch (38) is secured at the proximal end of shaft (40); while circuit board (39) is secured to the side of valve body (100). As also shown in FIG. 3, a valve plunger (90) is pivotably secured to a fork (66) at the proximal end of actuator (60) via a pin (66). A coil spring (36) is positioned in a recess (68) near fork (66). As best seen in FIGS. 6-7, actuator (60) also includes a button (62) with an underside (63). Underside (63) is positioned to actuate switch (38) when button (62) is depressed as described below. Actuator (60) also includes a set of integral pins (64) that pivotally couple actuator (60) with housings (32, 34). Thus, when button (62) is pressed downwardly, fork (66) pivots upwardly; and when button (62) returns upwardly, fork (66) pivots downwardly.

Figure 4:
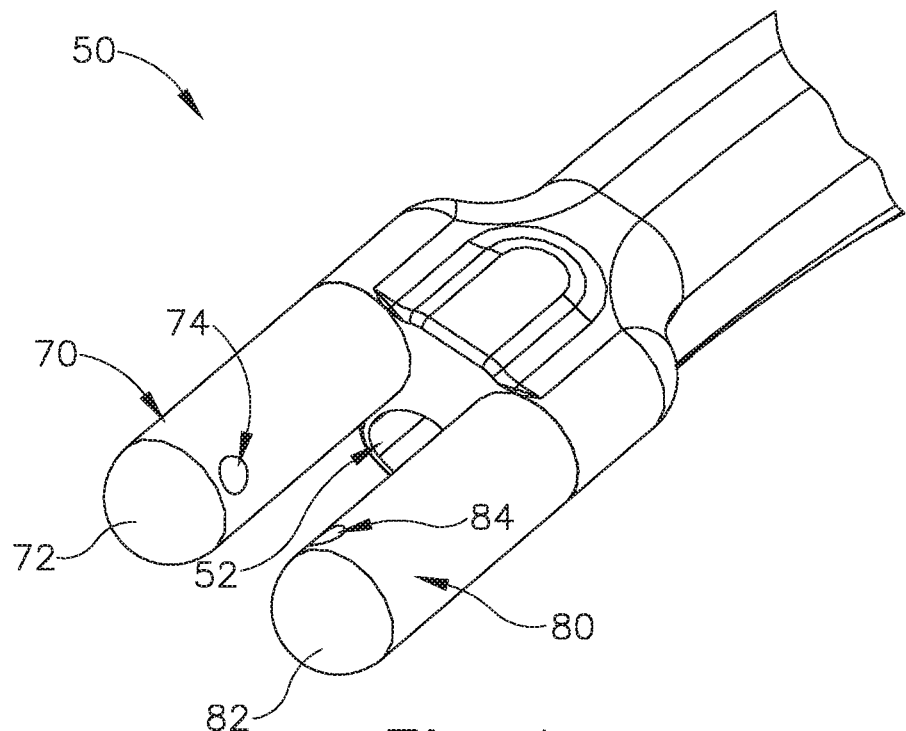
FIG. 4 depicts a perspective view of an end effector of the instrument of FIG. 1.
Figure 5:
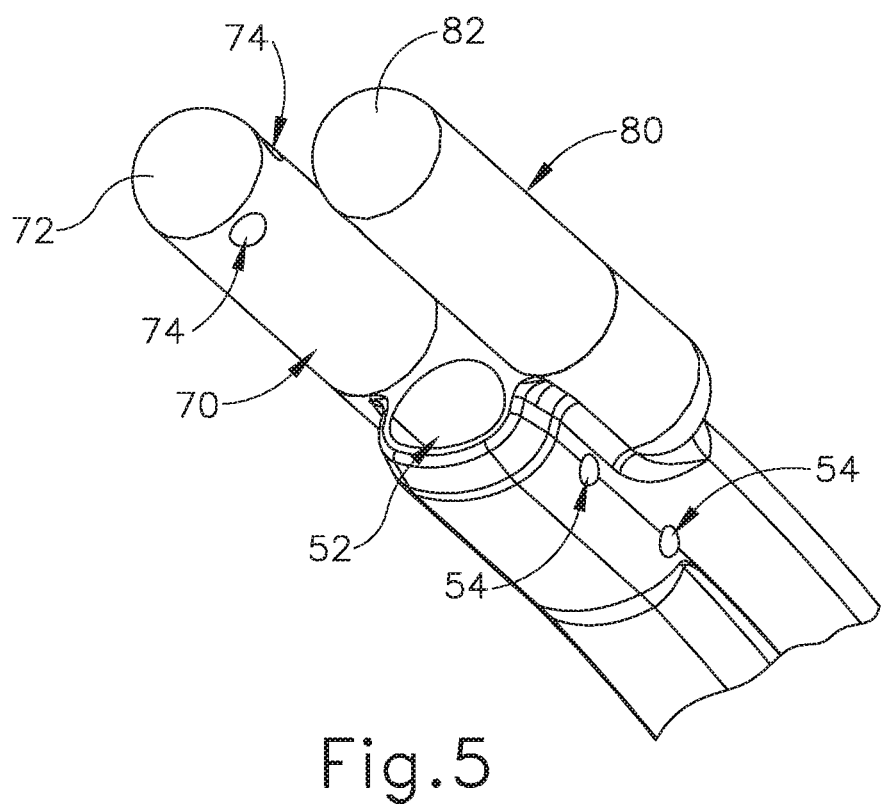
FIG. 5 depicts another perspective view of the end effector of FIG. 4.

As shown in FIGS. 4-5, the distal end of shaft (40) includes a distal suction opening (52) and a set of lateral suction openings (54). As also shown in FIGS. 4-5, each electrode (70, 80) includes a rounded distal end (72, 82) and a set of radial irrigation openings (74, 84). These features will be described in greater detail below.

Figure 8:
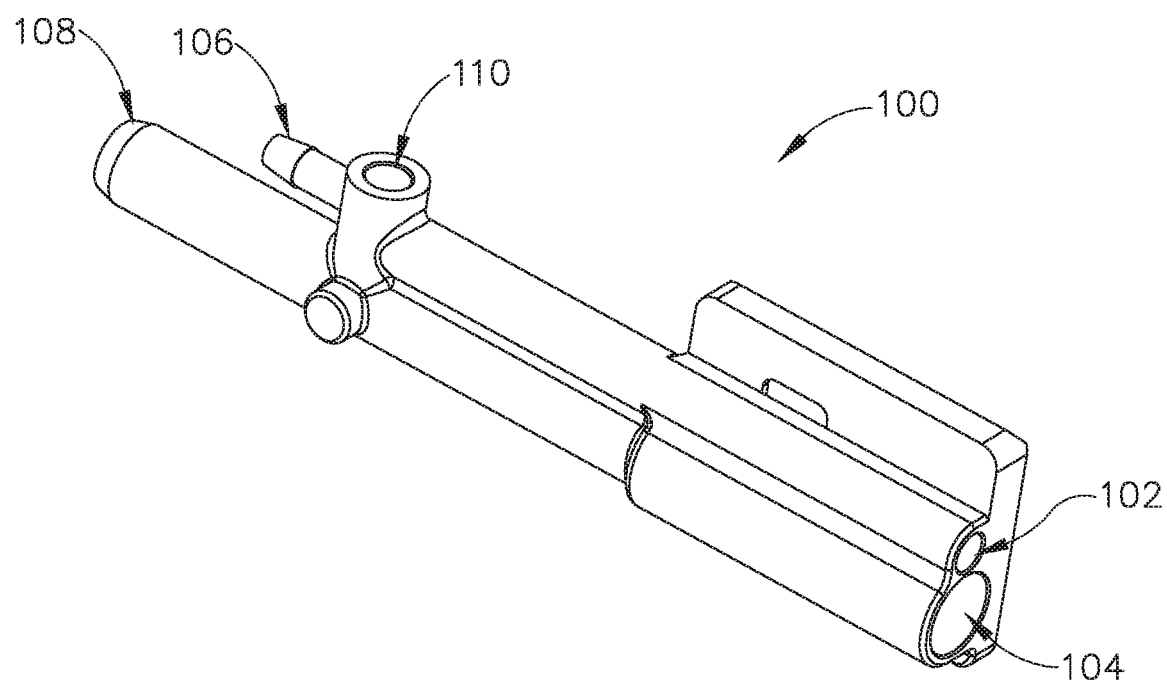
FIG. 8 depicts a perspective view of a valve body of the instrument of FIG. 1.
Figure 9:
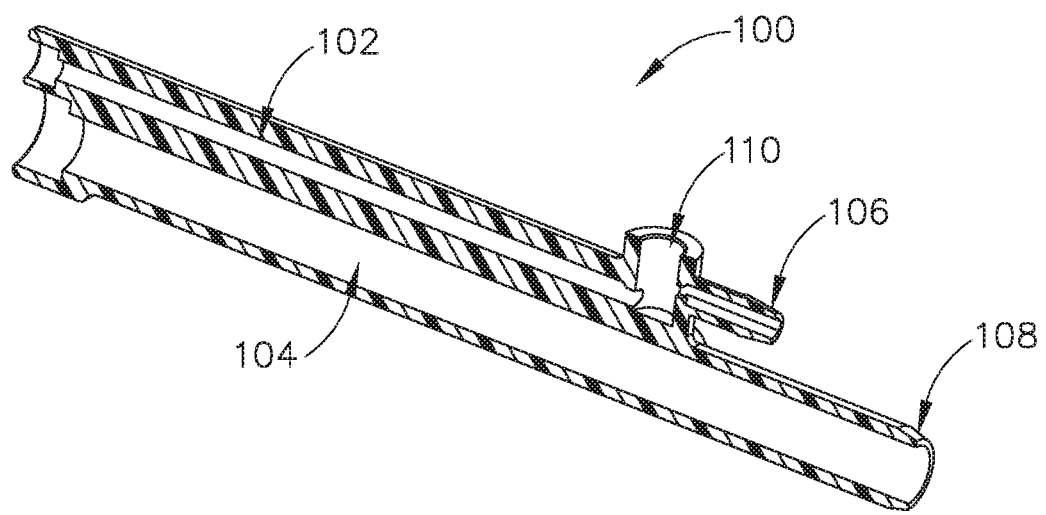
FIG. 9 depicts a side cross-sectional view of the valve body of FIG. 8.
Figure 12:
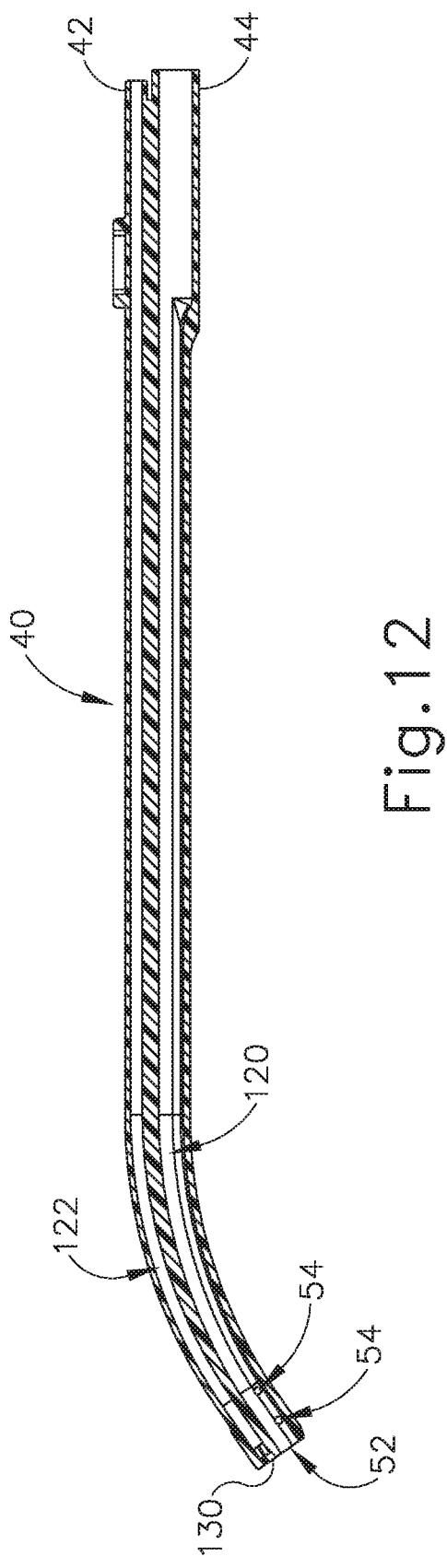
FIG. 12 depicts a side cross-sectional view of the shaft of FIG. 10, taken along line 12-12 of FIG. 10.
Figure 19A:
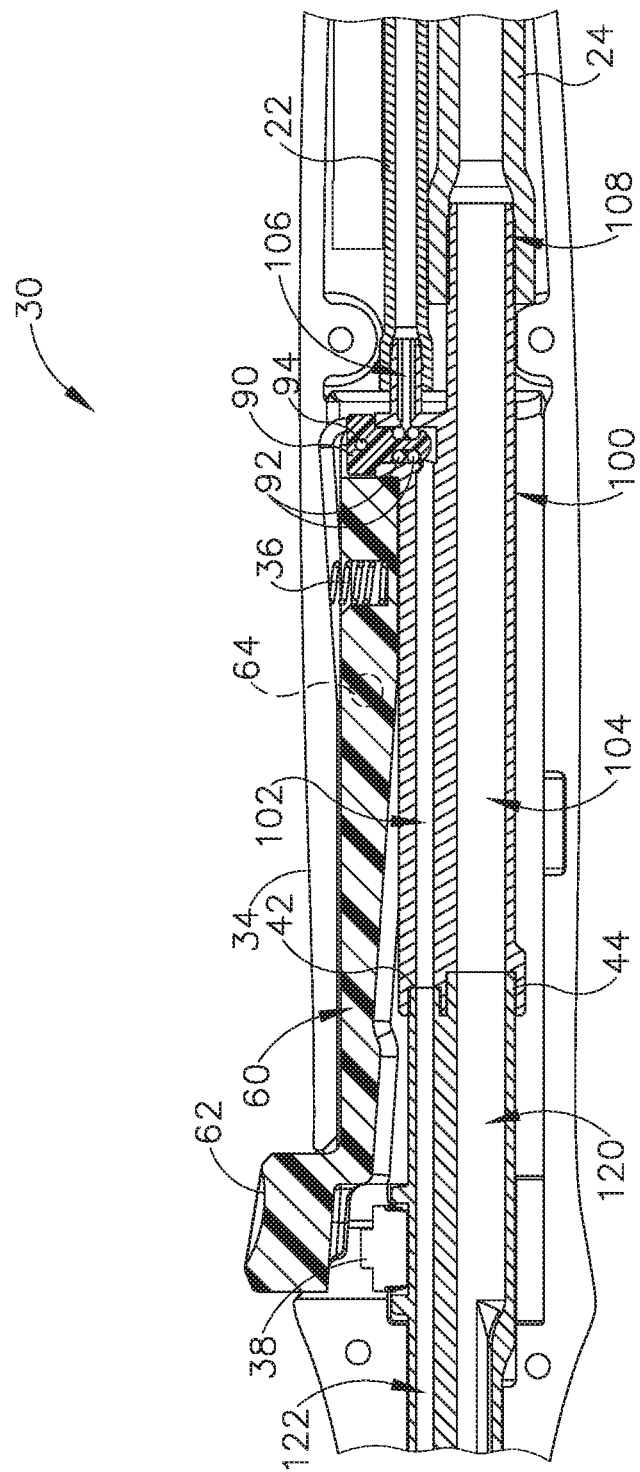
FIG. 19A depicts a side cross-sectional view of a handle assembly of the instrument of FIG. 1, with the actuator of FIG. 6 in a non-actuated state.
Figure 19B:
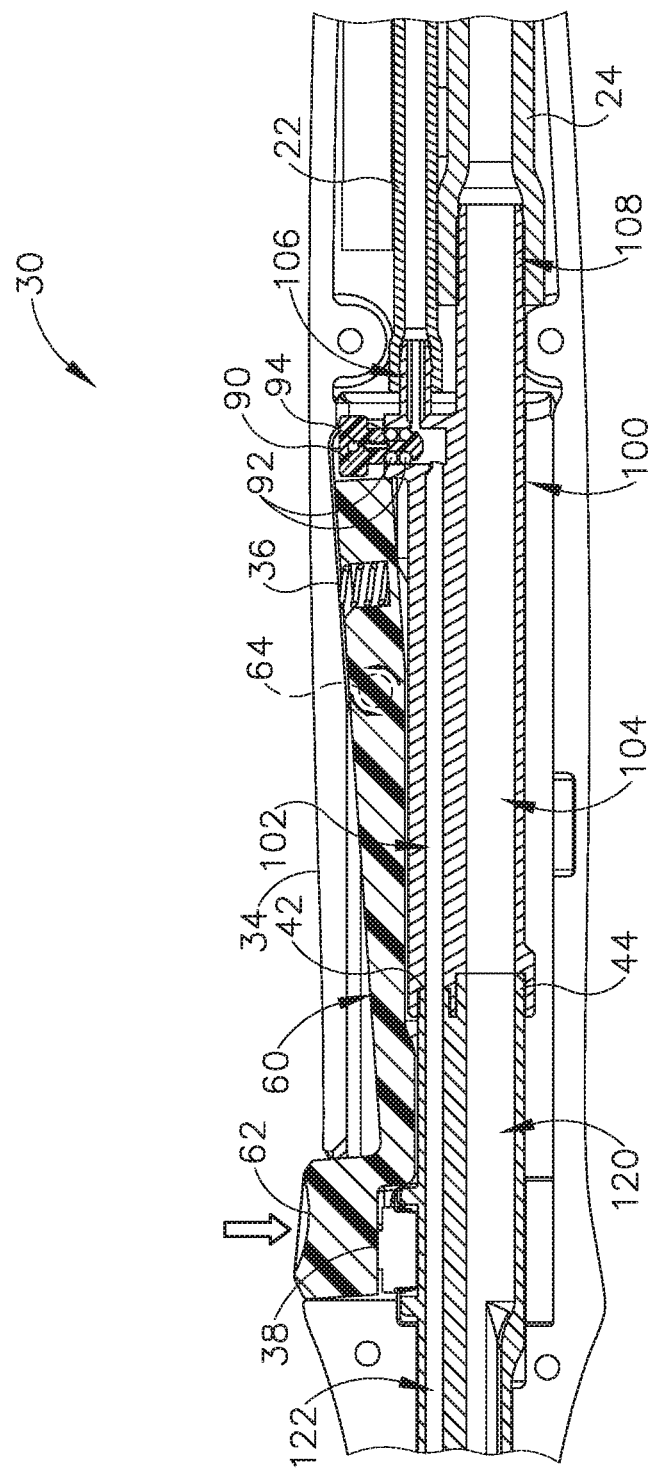
FIG. 19B depicts a side cross-sectional view of a handle assembly of the instrument of FIG. 1, with the actuator of FIG. 6 in an actuated state.

As shown in FIGS. 8-9, valve body (100) includes an upper lumen (102), a lower lumen (104), an upper proximal port (106), and a lower proximal port (108). Upper proximal port (106) is parallel with upper lumen (102) but is laterally offset relative to upper lumen (102). A transverse valve bore (110) is located at the proximal end of valve body (100), adjacent to upper proximal port (106). Valve bore (110) provides a path for fluid communication between upper proximal port (106) and an upper lumen (102). Lower lumen (104) is coaxial with lower proximal port (108), such that lower lumen (104) is in constant fluid communication with lower proximal port (108). As shown in FIGS. 19A-19B, upper proximal port (106) is coupled with saline tube (22) while lower proximal port (108) is coupled with suction tube (24). By way of example only, ports (106, 108) may include barbs and/or other features configured to maintain a secure, fluid tight fitting with respective tubes (22, 24).

As shown in FIGS. 10-14, the distal portion of shaft (40) is gradually bent, which may promote visibility and access for end effector (50) with respect to the targeted tissue. As also shown in FIGS. 10-14, shaft (40) includes an upper proximal port (42) in fluid communication with an upper lumen (122); and a lower proximal port (44) in fluid communication with a lower lumen (120). Upper proximal port (42) is positioned and configured to couple with upper lumen (102) of valve body (100), such that upper lumen (122) of shaft (40) receives saline communicated through upper lumen (102) of valve body (100). Lower proximal port (44) is positioned and configured to couple with lower lumen (104) of valve body (100), such that lower lumen (120) of shaft (40) receives suction communicated through lower lumen (104) of valve body (100). Lower lumen (120) is also in fluid communication with distal suction opening (52) and lateral suction openings (54), such that suction communicated through lower lumen (120) is communicated through openings (52, 54).

Figure 14:
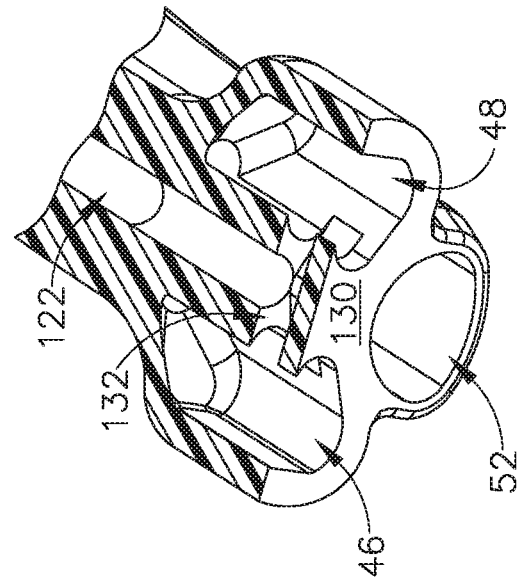
FIG. 14 depicts a cross-sectional view of the distal end of the shaft of FIG. 10, taken along line 14-14 of FIG. 13.
Figure 13:
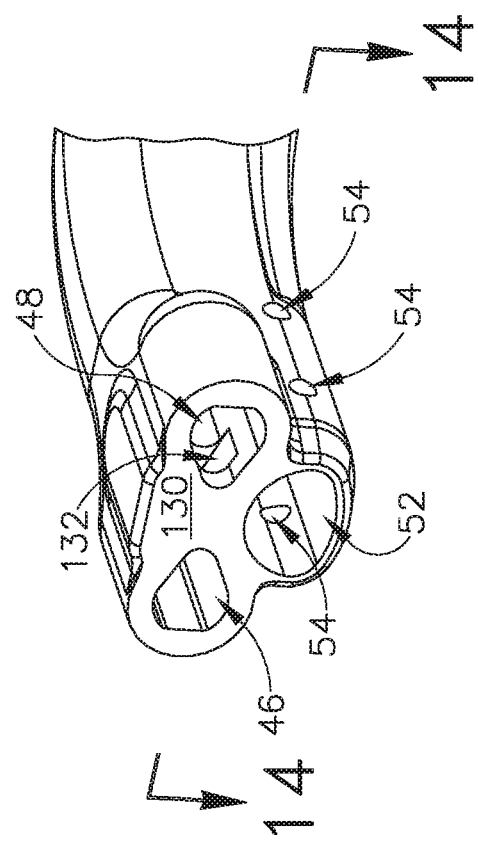
FIG. 13 depicts an enlarged perspective view of a distal end of the shaft of FIG. 10.
Figure 15:
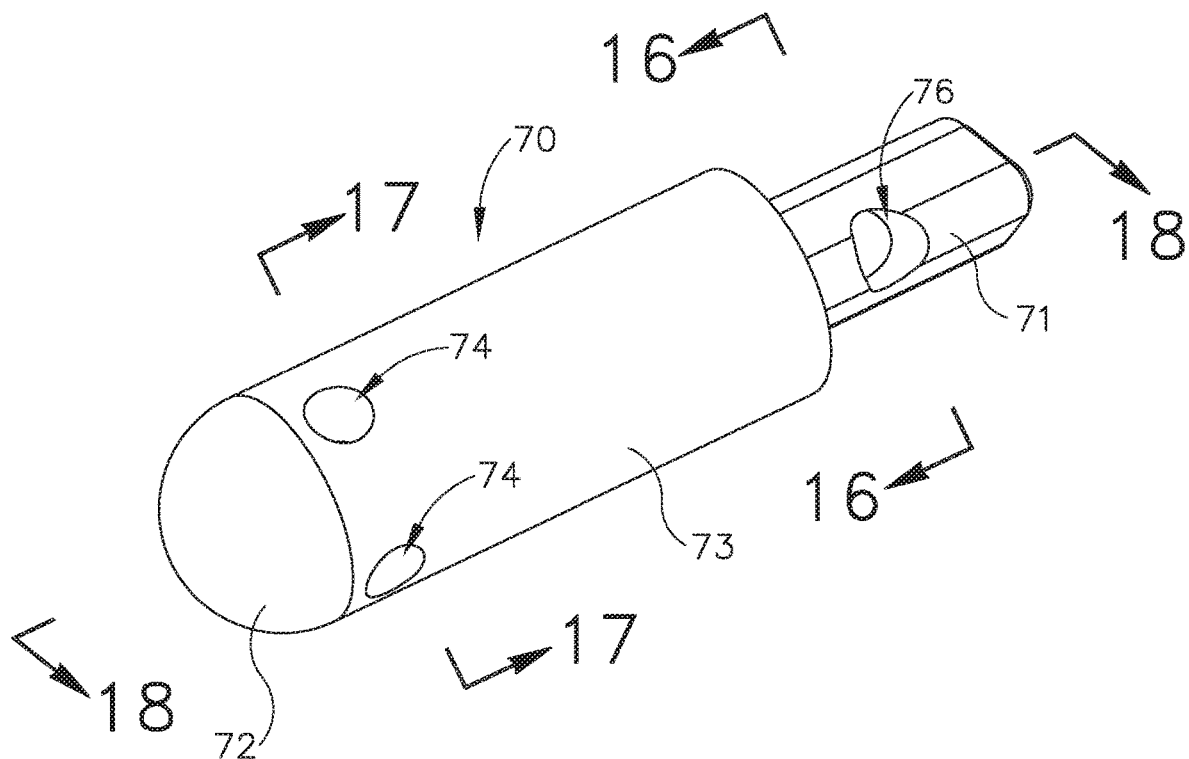
FIG. 15 depicts a perspective view of an electrode of the end effector of FIG. 4.

As shown in FIG. 14, the distal end of upper lumen (122) terminates in a transverse passageway (132). Passageway (132) laterally terminates in sockets (46, 48). Sockets (46, 48) are configured to receive respective electrodes (70, 80). FIGS. 15-18 show electrode (70) in greater detail. Electrode (80) is configured like electrode (70), but as a mirror image. Electrode (80) thus has structures like those described below with respect to electrode (70). As shown, electrode (70) of this example comprises a base (71) extending proximally from a body (73). Base (71) is configured to fit in socket (46) of shaft (40). By way of example only, base (71) may be fixedly secured in socket (46) by an interference fit, adhesive, and/or using any other suitable features or techniques. Base (71) and socket (46) have a generally triangular profile in this example, though any other suitable shapes may be used. Body (73) of the present example is cylindrical, with a circular profile, though any other suitable shapes may be used. Distal end (72) is configured as a hemisphere in the present example, though any other suitable shape may be used.

Figure 16:
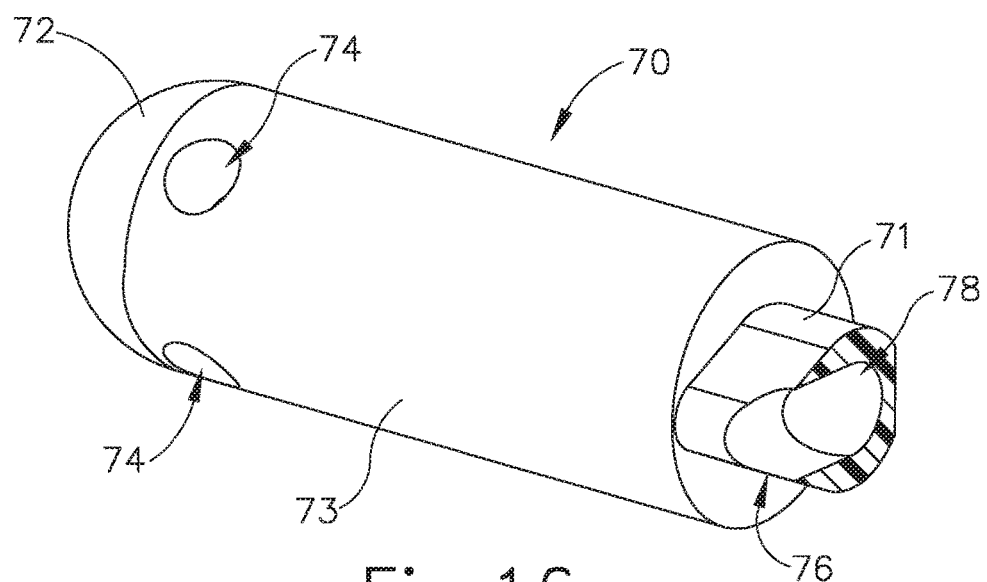
FIG. 16 depicts a perspective cross-sectional view of the electrode of FIG. 15, taken along line 16-16 of FIG. 15.
Figure 17:
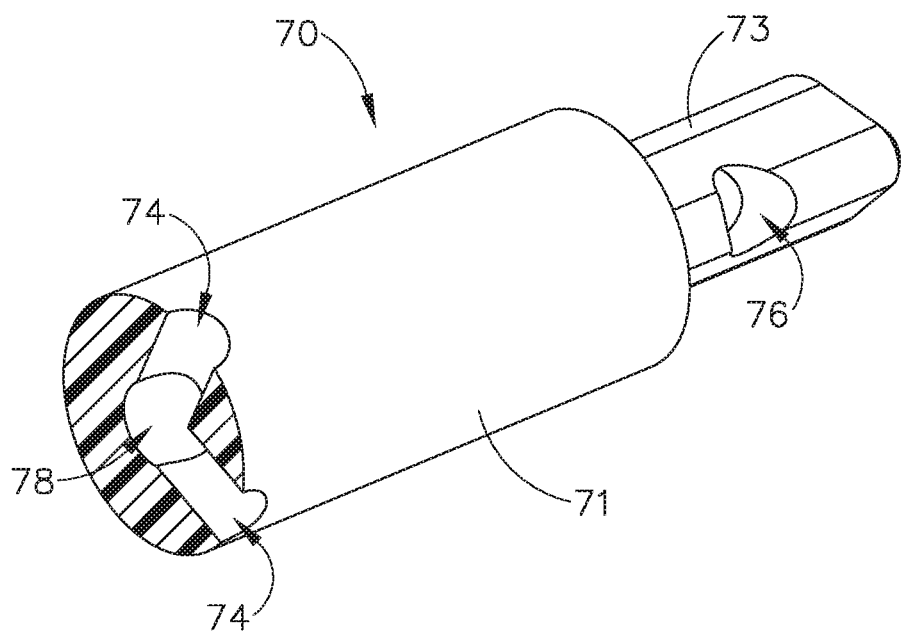
FIG. 17 depicts another perspective cross-sectional view of the electrode of FIG. 15, taken along line 17-17 of FIG. 15.
Figure 18:
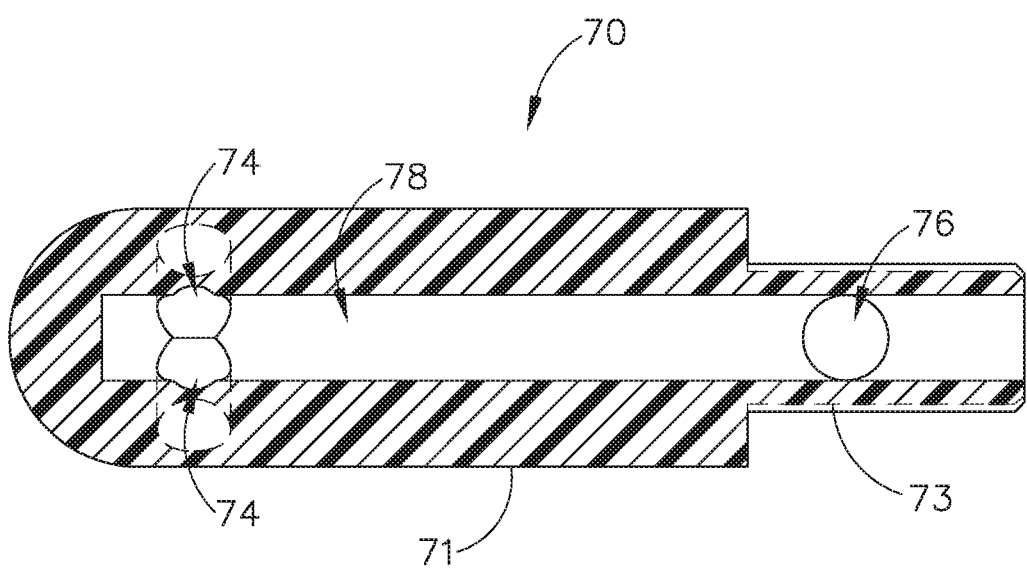
FIG. 18 depicts a side cross-sectional view of the electrode of FIG. 15, taken along line 18-18 of FIG. 15.

As best seen in FIGS. 16-18, a bore (78) extends longitudinally through a portion of the length of electrode (70). A transverse passageway (76) is formed through base (71) and is in fluid communication with bore (78). Transverse passageway (76) is configured to align with transverse passageway (132) in socket (46) when base (71) is fully seated in socket (46). Thus, when saline is communicated through upper lumen (122) of shaft (40), the saline will enter bore (78) of electrode (70) via transverse passageways (76, 132). A pair of radial irrigation openings (74) are located just proximal to distal end (72) and are also in fluid communication with bore (78). Thus, when saline is communicated through bore (78) as described above, the saline will exit through radial irrigation openings (74). As shown in FIGS. 4-5, radial irrigation openings (74, 84) are oriented generally toward the space between electrodes (70, 80). In other variations, a different number of radial irrigation openings (74, 84), and/or radial irrigation openings (74, 84) are positioned at different orientations than those shown.

As shown in FIGS. 19A-19B, valve plunger (90) is slidably disposed in transverse valve bore (110) of valve body (100). A pair of o-rings (92) are secured to valve plunger (90). When actuator (60) is in a non-actuated state (i.e., when button (62) is not being depressed), coil spring (36) resiliently urges the proximal end of actuator (60) downwardly, thereby urging valve plunger (90) to a downward position within transverse valve bore (110). With valve plunger (90) in this position, as shown in FIG. 19A, o-rings (92) provide a seal between upper proximal port (106) and upper lumen (102), thereby preventing saline from being communicated from upper proximal port (106) to upper lumen (102). When the operator presses button (62) downwardly to the position shown in FIG. 19B, underside (63) actuates switch (38), and the proximal end of actuator (60) pivots upwardly about pins (64). This in turn pulls valve plunger (90) to an upward position, where o-rings (92) clear proximal port (106) and thereby enable fluid communication from proximal port (106) to upper lumen (102). When the operator releases button (62), coil spring (36) urges actuator (60) back to the pivotal position shown in FIG. 19A, thereby closing off the fluid path from proximal port (106) to upper lumen (102); and thereby disengaging switch (38).

In an exemplary use, an operator may grasp handle assembly (40) and thereby manipulate shaft (40) to position end effector (50) adjacent to tissue with one or more bleeding vessels (e.g., along parenchyma of a fractured liver, etc.). The operator may then depress button (62) of actuator (60). This will simultaneously activate electrodes (70, 80) with bipolar RF energy while also providing saline from saline source (14) to radial irrigation openings (74, 84) of electrodes (70, 80). This saline expelled through radial irrigation openings (74, 84) promotes electrical conductivity between electrodes (70, 80) and the tissue that is engaged by electrodes (70, 80). The applied bipolar RF energy eventually seals the bleeding vessels. The operator then releases button (62) to cease RF activation of electrodes (70, 80); and to simultaneously cease delivery of saline to the surgical site. Before, during, and/or after the delivery of RF energy and saline to tissue, instrument (10) may also provide suction from suction source (16) to the surgical site via openings (52, 54). This suction may draw away saline, blood, other bodily fluids, and/or debris. In some versions, the suction is constant. In some other versions, the suction is selectively activated by a button on handle assembly (30), by a footswitch (not shown), or by some other means.

II. Exemplary Alternative Electrosurgical Shaft Assembly and End Effector

Figure 20:
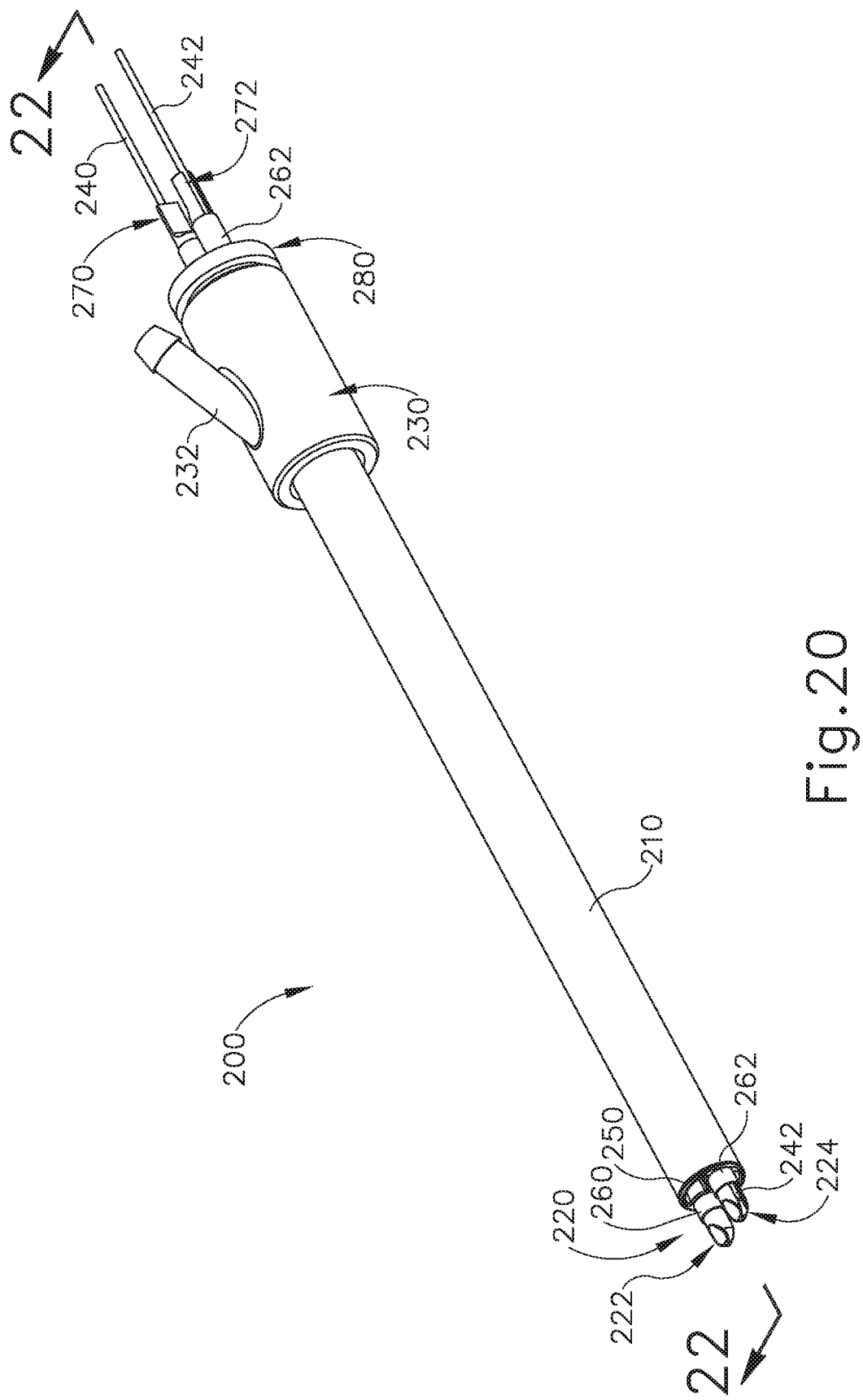
FIG. 20 depicts a perspective view of an exemplary alternative shaft assembly of another exemplary electrosurgical instrument.
Figure 21:
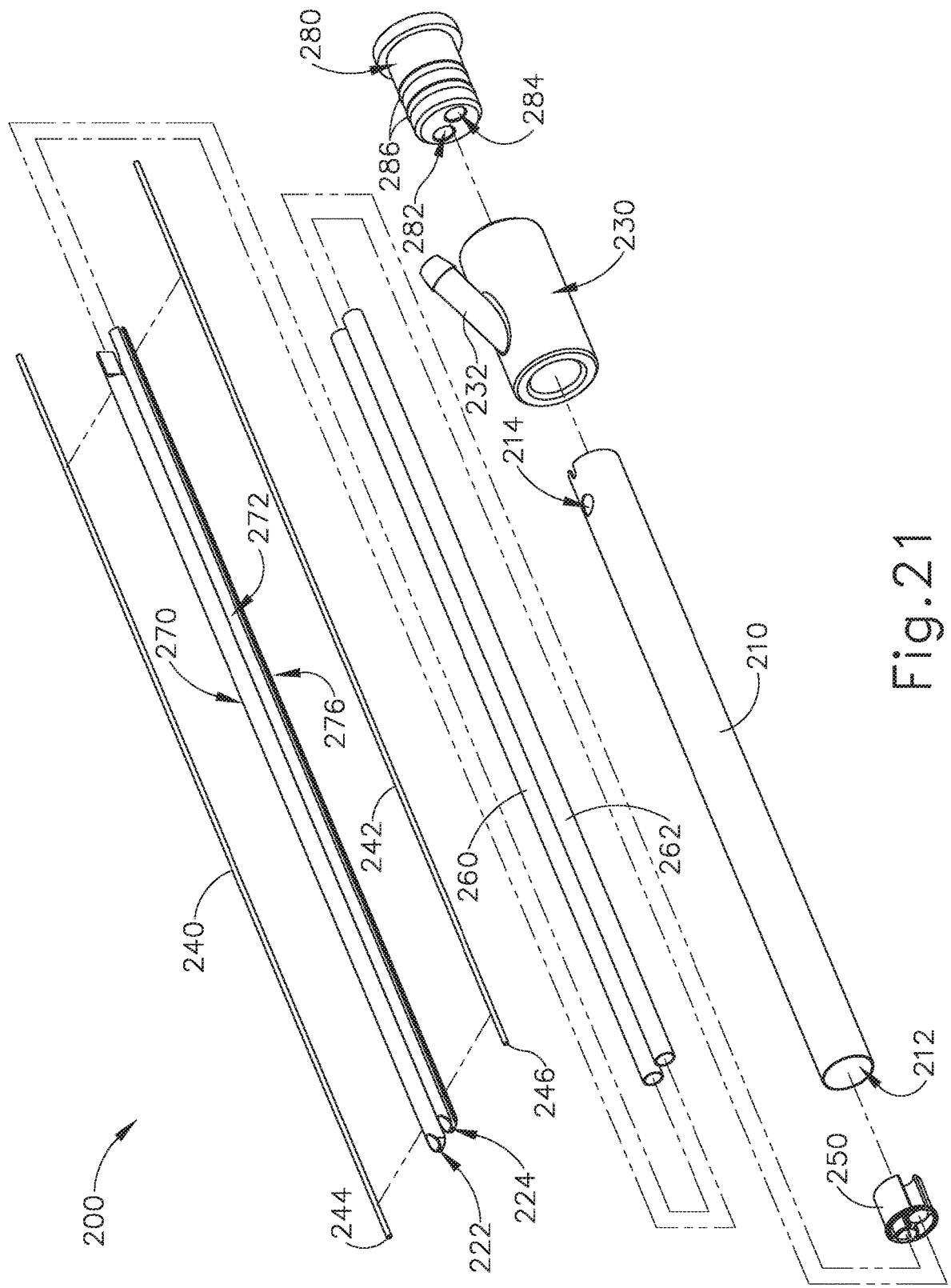
FIG. 21 depicts an exploded perspective view of the shaft assembly of FIG. 20.
Figure 22:
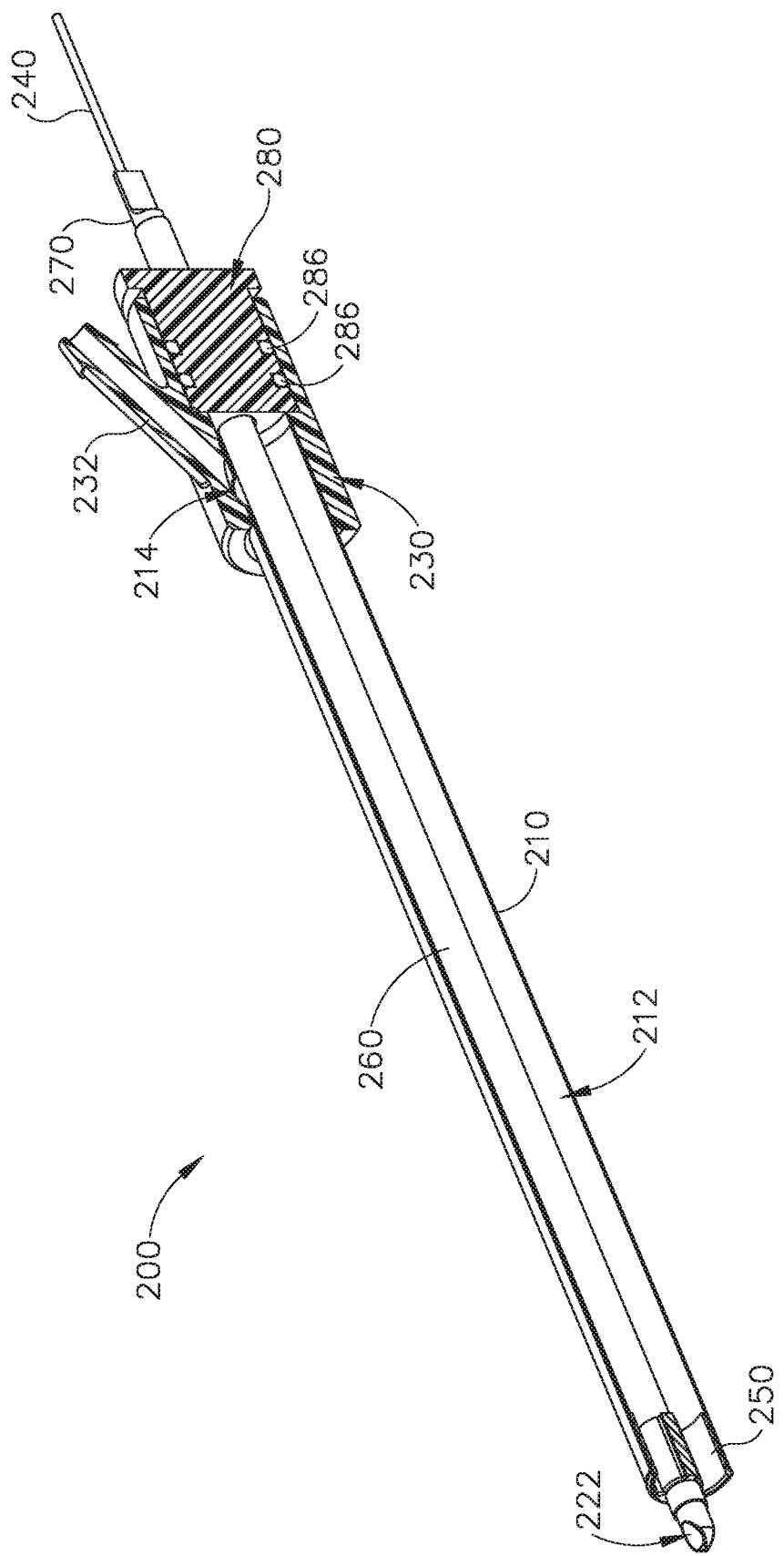
FIG. 22 depicts a side cross-sectional view of the shaft assembly of FIG. 20, taken along line 22-22 of FIG. 20.

FIGS. 20-22 show an exemplary alternative shaft assembly (200) and end effector (220) that may be incorporated into instrument (10). While shaft assembly (200) is shown as being straight along its full length, some variations may include a bent region, like shaft (40) described above or otherwise. Shaft assembly (200) of this example comprises an outer sheath (210), a port body (230), an end cap (250), and a plug (280). As best seen in FIG. 21, a pair of electrode rods (270, 272) are disposed in respective sheaths (260, 262). Each electrode rod (270, 272) is coupled with an electrical power source, like electrical power source (12) described above, such that electrode rods (270, 272) may be used to communicate bipolar RF electrosurgical energy as described below. In the present example, each sheath (260, 262) is formed of an electrically insulative material. For instance, each sheath (260, 262) may comprise a heat shrink wrap.

Each electrode rod (270, 272) includes a lateral recess (274, 276) extending along the length of electrode rod (270, 272). A corresponding irrigation tube (240, 242) is positioned in each lateral recess (274, 276). Irrigation tubes (240, 242) are in fluid communication with a source of saline, such as saline source (14). Sheath (260) captures irrigation tube (240) in lateral recess (274); while sheath (262) captures irrigation tube (242) in lateral recess (276). The assembly of electrode rod (270), irrigation tube (240), and sheath (260) is parallel with (yet laterally offset from) the assembly of electrode rod (272), irrigation tube (242), and sheath (262). The distal portions of these assemblies are supported within end cap (250). The proximal portions of these assemblies are disposed in corresponding passageways (282, 284) of plug (280), such that plug (280) supports the proximal portions of these assemblies.

As best seen in FIG. 21, the proximal portion of outer sheath (210) includes a lateral opening (214) in fluid communication with a lumen (212) defined by outer sheath (210). When the proximal portion of outer sheath (210) is fully seated in port body (230), an oblique suction port (232) aligns with lateral opening (214). Lateral opening (214) thus provides a path for fluid communication between suction port (232) and lumen (212) of hollow interior of outer sheath (210). Suction port (232) may be further coupled with a source of suction, like suction source (16) described above. As best seen in FIGS. 21-22, plug (280) is configured to fit in the proximal end of port body (230). A pair of o-rings (286) provide a fluid-tight seal within port body (230). Moreover, plug (280) elastomerically bears against sheaths (260, 262) disposed in passageways (282, 284). Plug (280) thus prevents suction from leaking through the proximal end of port body (230).

Figure 23:
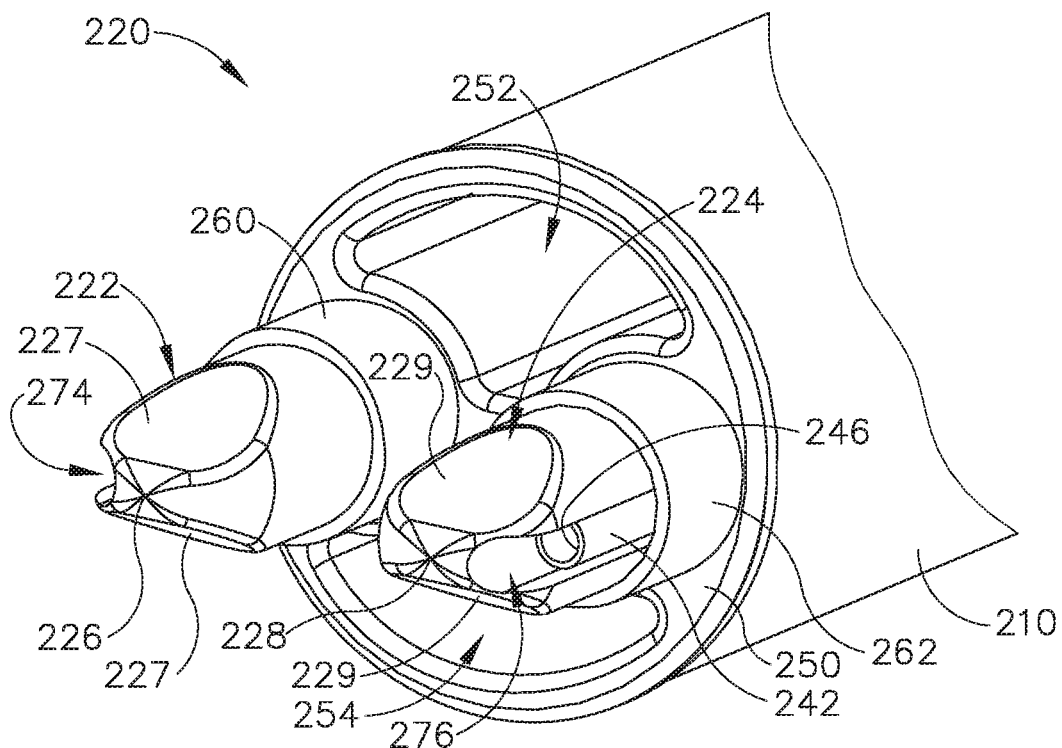
FIG. 23 depicts a perspective view of an end effector of the shaft assembly of FIG. 20.

As best seen in FIGS. 23-26, end effector (220) includes a pair of electrodes (222, 224). Electrode (222) is a unitary feature of the distal end of electrode rod (270); while electrode (224) is a unitary feature of the distal end of electrode rod (272). Electrodes (222, 224) are exposed relative to respective sheaths (260, 262). Electrode (222) includes a pair of flat surfaces (227) that taper toward each other along the distal direction, with a distal point (226). Electrode (224) includes a pair of flat surfaces (228) that taper toward each other along the distal direction, with a distal point (228). As best seen in FIG. 23, the distal end (246) of each tube (240, 242) is exposed relative to the distal end of the corresponding sheath (260, 262).

Figure 24:
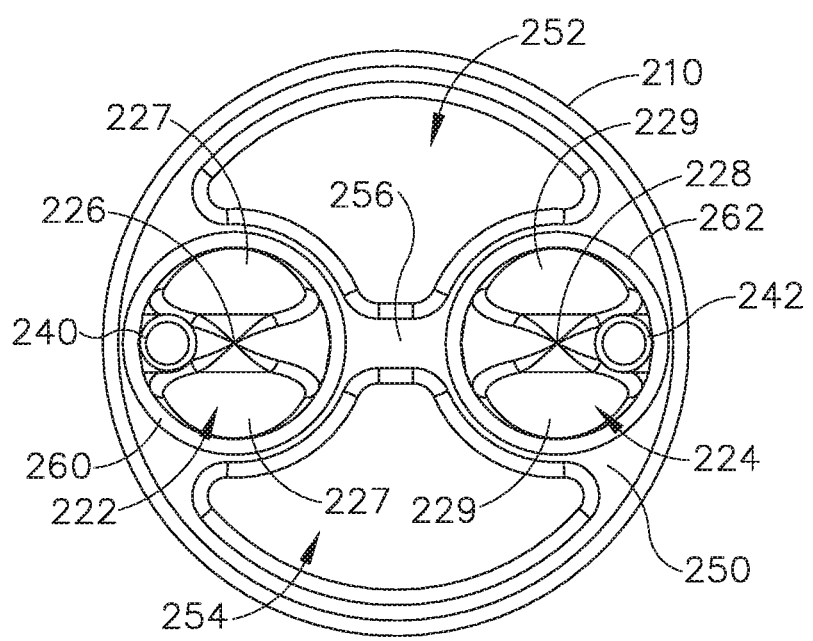
FIG. 24 depicts an end view of the end effector of FIG. 23.
Figure 25:
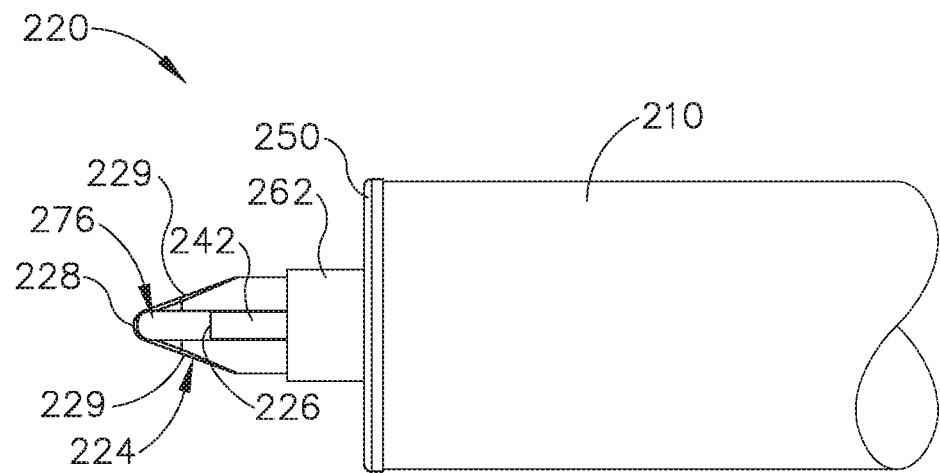
FIG. 25 depicts a side elevational view of the end effector of FIG. 23.
Figure 26:
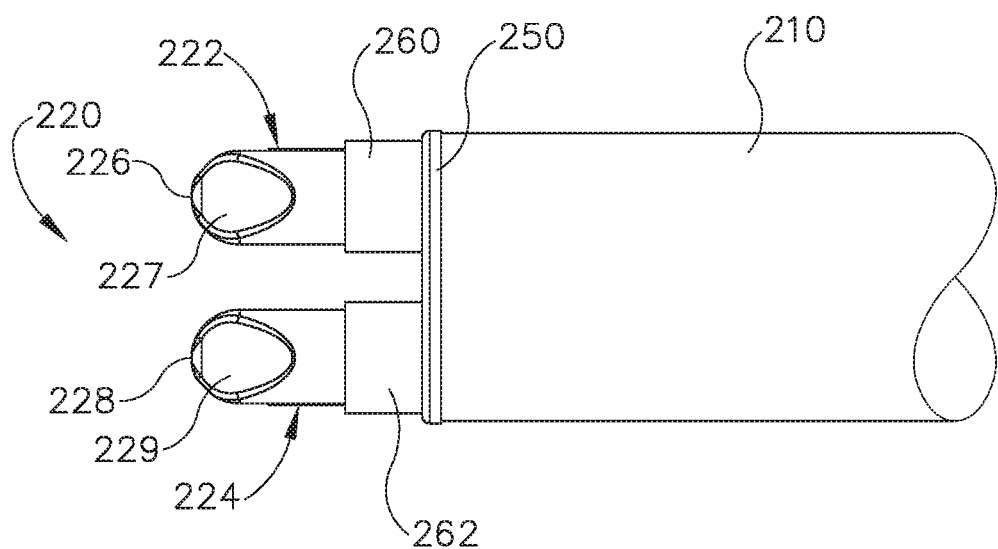
FIG. 26 depicts a top plan view of the end effector of FIG. 23.

As best seen in FIGS. 23-24, end cap (250) includes an upper opening (252) and a lower opening (254), separated by a web (256). Web (256) extends laterally in the region between electrodes (222, 224). Openings (252, 254) are in fluid communication with lumen (212) of outer sheath (210), such that openings (252, 254) may communicate suction delivered to lumen (212) from a suction source coupled with suction port (232).

In an exemplary use, an operator may grasp a handle assembly (not shown) that is coupled with shaft assembly (200) and thereby manipulate shaft assembly (200) to position end effector (220) adjacent to tissue with one or more bleeding vessels (e.g., along parenchyma of a fractured liver, etc.). The operator may then activate one or more user input features (e.g., like actuator (60), etc.) to activate electrodes (222, 224) with bipolar RF energy while also delivering saline to the tissue via distal ends (246) of tubes (240, 242). This saline expelled through distal ends (246) of tubes (240, 242) promotes electrical conductivity between electrodes (222, 224) and the tissue that is engaged by electrodes (222, 224). The applied bipolar RF energy eventually seals the bleeding vessels. The operator then ceases RF activation of electrodes (222, 224) and delivery of saline to the surgical site. Before, during, and/or after the delivery of RF energy and saline to tissue, shaft assembly (200) may also provide suction to the surgical site via openings (252, 254). This suction may draw away saline, blood, other bodily fluids, and/or debris. In some versions, the suction is constant. In some other versions, the suction is selectively activated by a user input feature.

III. Exemplary Alternative End Effectors

In some scenarios, it may be desirable to promote better dispersion of saline on and around electrodes and adjacent tissue as the electrodes deliver RF electrosurgical energy to the tissue. To that end, FIGS. 27-36 show various exemplary alternative end effector configurations. Any of the following end effector configurations may be readily incorporated into instrument (10) or shaft assembly (200), in place of end effector (50) or end effector (220). Alternatively, the following end effector configurations may be incorporated into various other kinds of instrumentation as will be apparent to those of ordinary skill in the art in view of the teachings herein.

Figure 27:
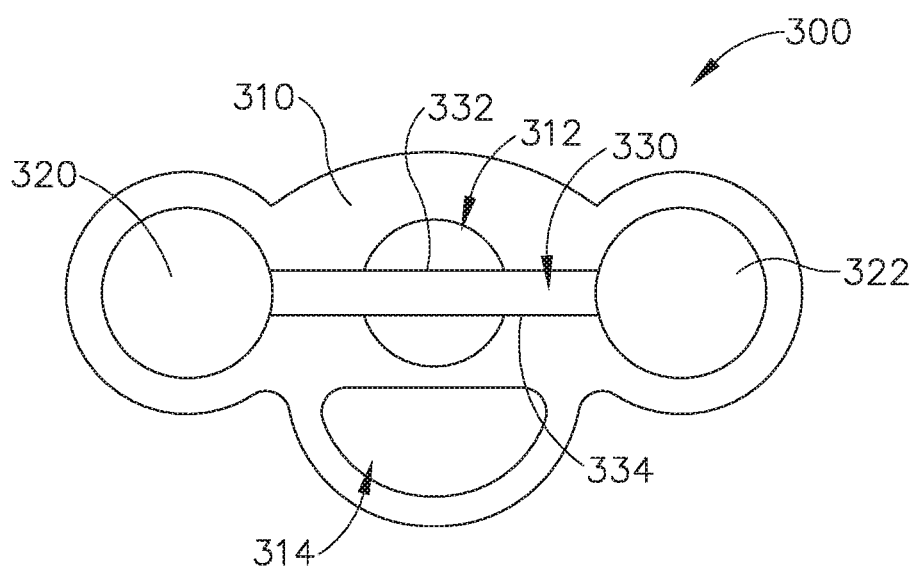
FIG. 27 depicts an end view of an exemplary alternative end effector.
Figure 28:
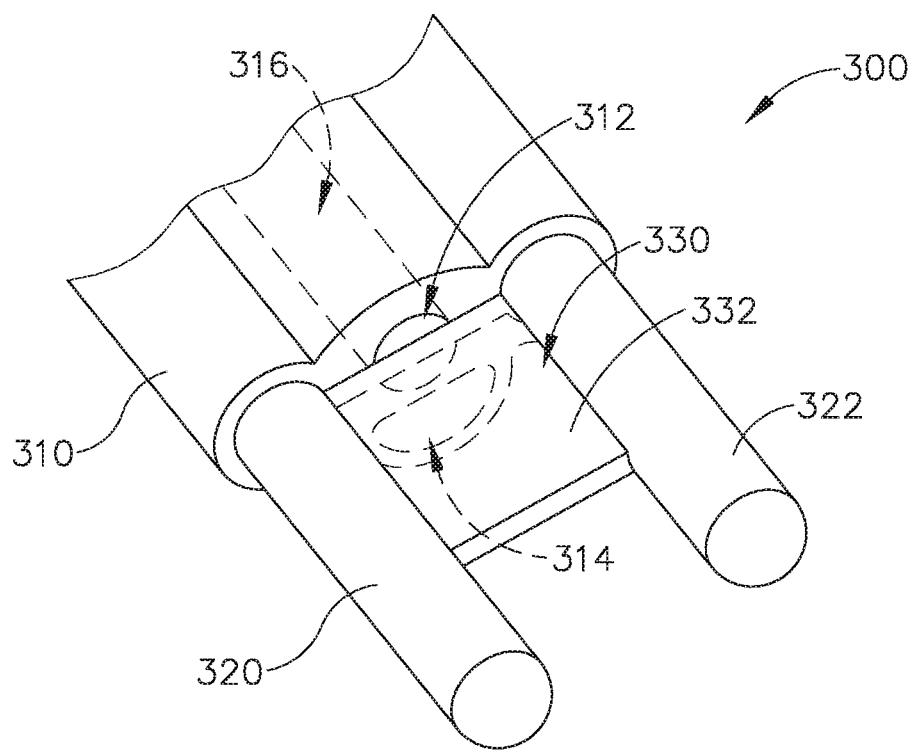
FIG. 28 depicts a perspective view of the end effector of FIG. 27.

FIGS. 27-28 show an exemplary alternative end effector (300) that comprises a pair of electrodes (320, 322) at the distal end of a shaft (310). Shaft (310) includes an irrigation lumen (316) distally terminating at an irrigation opening (312). Shaft (310) also includes a suction opening (314). A web (330) extends laterally between electrodes (320, 322). Web (330) is formed of an electrically non-conductive material. In some versions, web (330) contacts both electrodes (320, 322). In some other versions, web (330) does not contact either electrode (320, 322), such that gaps are formed laterally between the outer lateral edges of web (330) and electrodes (320, 322). As best seen in FIG. 27, web (330) is positioned to bisect the space just distal to irrigation opening (312). Thus, as saline is expelled distally from irrigation opening (312), the flow of saline is split by web (330), flowing along upper surface (332) and lower surface (334) of web (330). As saline is expelled distally from irrigation opening (312), electrodes (320, 322) may be activated to apply RF electrosurgical energy to tissue that is in contact with electrodes (320, 322), while suction may be applied to the surgical site via suction opening (314).

Figure 29:
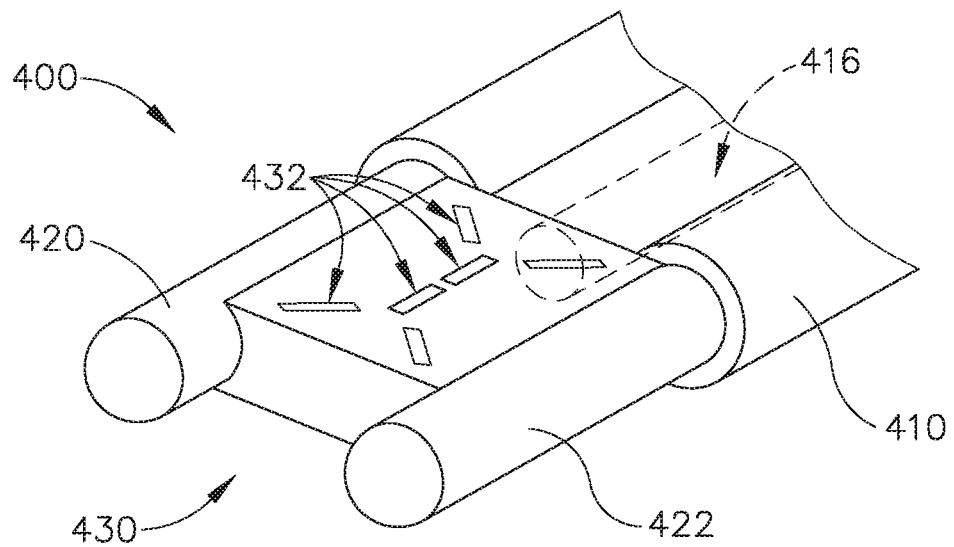
FIG. 29 depicts a perspective view of another exemplary alternative end effector.

FIG. 29 shows another exemplary alternative end effector (400) that comprises a pair of electrodes (420, 422) at the distal end of a shaft (410). Shaft (410) includes an irrigation lumen (416). While not shown, shaft (410) may also include one or more suction openings, similar to those described above. A web (430) extends laterally between electrodes (420, 422). Web (430) is formed of an electrically non-conductive material. In some versions, web (430) contacts both electrodes (420, 422). In some other versions, web (430) does not contact either electrode (420, 422), such that gaps are formed laterally between the outer lateral edges of web (430) and electrodes (420, 422).

Web (430) of the present example includes a set of irrigation openings (432). Irrigation openings (432) are in fluid communication with a hollow interior region (not shown) of web (430), which is further in fluid communication with irrigation lumen (416). Irrigation openings (432) of the present example are rectangular and are arranged such that two irrigation openings (432) are parallel with the longitudinal axis of shaft (410) while four other irrigation openings (432) are obliquely oriented relative to the longitudinal axis of shaft. Alternatively, irrigation openings (432) may have any other suitable orientation and arrangement. While irrigation openings (432) are only shown on the top of web (430), the bottom of web (430) may also include irrigation openings (432). As saline is communicated distally through irrigation lumen (416), the saline is expelled through irrigation openings (432). As saline is expelled through irrigation openings (432), electrodes (420, 422) may be activated to apply RF electrosurgical energy to tissue that is in contact with electrodes (420, 422), while suction may be applied to the surgical site via one or more suction openings (not shown) of shaft (410).

Figure 30:
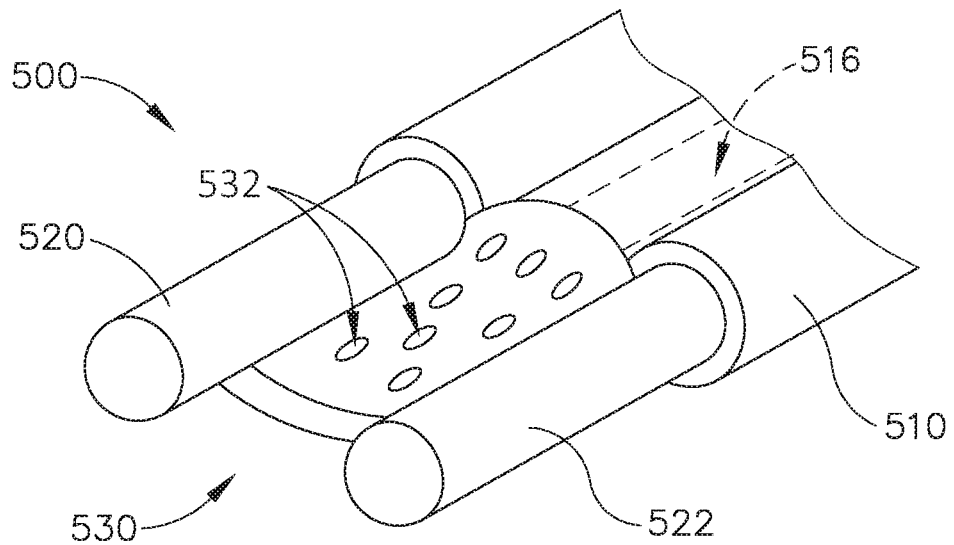
FIG. 30 depicts a perspective view of another exemplary alternative end effector.

FIG. 30 shows another exemplary alternative end effector (500) that comprises a pair of electrodes (520, 522) at the distal end of a shaft (510). Shaft (510) includes an irrigation lumen (516). While not shown, shaft (510) may also include one or more suction openings, similar to those described above. A web (530) extends laterally between electrodes (520, 522). Web (530) is formed of an electrically non-conductive material. In some versions, web (530) contacts both electrodes (520, 522). In some other versions, web (530) does not contact either electrode (520, 522), such that gaps are formed laterally between the outer lateral edges of web (530) and electrodes (520, 522).

Web (530) of the present example includes a set of irrigation openings (532). Irrigation openings (532) are in fluid communication with a hollow interior region (not shown) of web (530), which is further in fluid communication with irrigation lumen (516). Irrigation openings (432) of the present example are elliptical and are arranged in a plurality of linear arrays that are parallel with the longitudinal axis of shaft (510). Alternatively, irrigation openings (532) may have any other suitable orientation and arrangement. While irrigation openings (532) are only shown on the top of web (530), the bottom of web (530) may also include irrigation openings (532). As saline is communicated distally through irrigation lumen (516), the saline is expelled through irrigation openings (532). As saline is expelled through irrigation openings (532), electrodes (520, 522) may be activated to apply RF electrosurgical energy to tissue that is in contact with electrodes (520, 522), while suction may be applied to the surgical site via one or more suction openings (not shown) of shaft (510).

Figure 31:
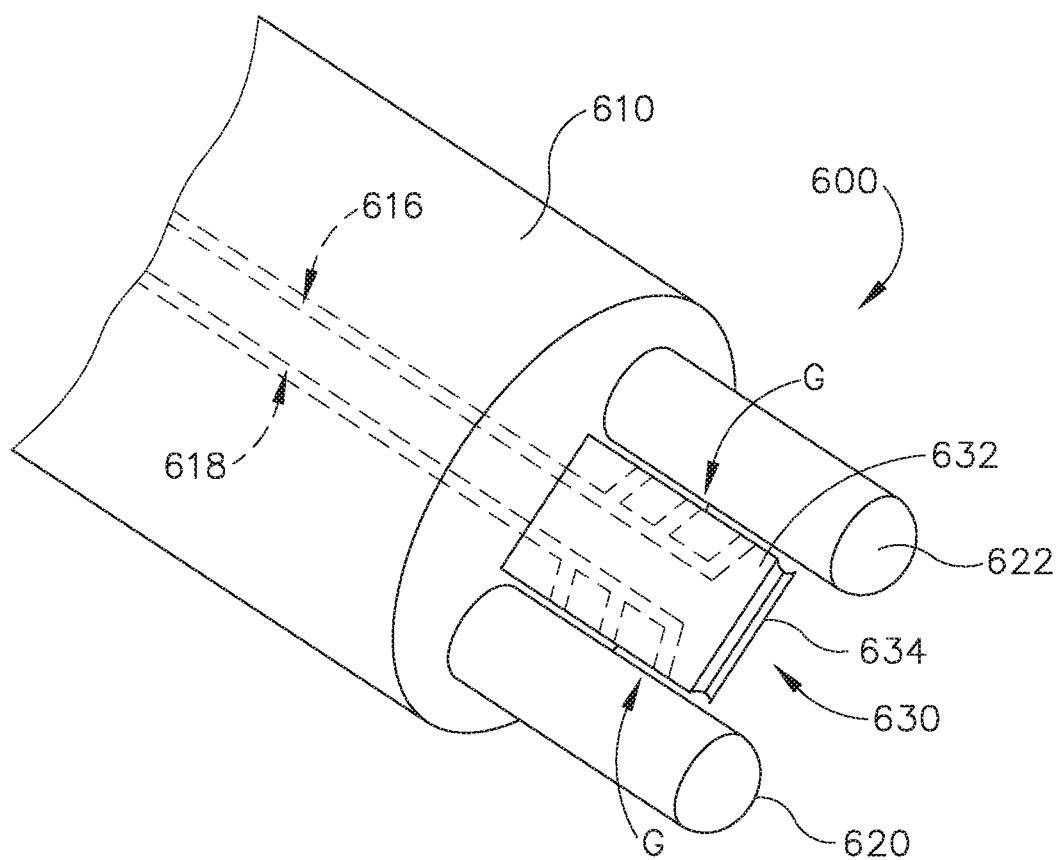
FIG. 31 depicts a perspective view of another exemplary alternative end effector.

FIG. 31 shows another exemplary alternative end effector (600) that comprises a pair of electrodes (620, 622) at the distal end of a shaft (610). Shaft (610) includes a pair of irrigation lumens (616, 618). While not shown, shaft (610) may also include one or more suction openings, similar to those described above. A web (630) extends laterally between electrodes (620, 622). Web (630) is formed of an electrically non-conductive material. In the present example, web (630) does not contact either electrode (620, 622), such that gaps (G) are formed laterally between the outer lateral edges of web (630) and electrodes (620, 622).

Figure 32:
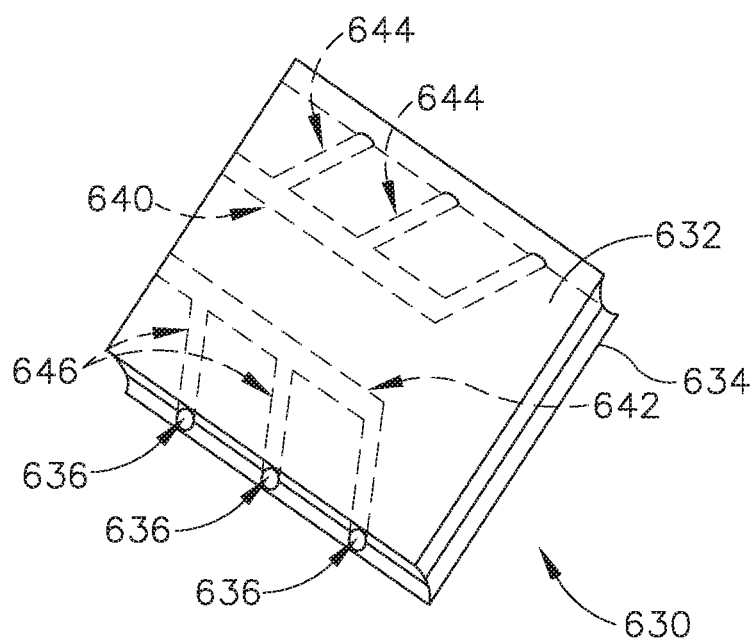
FIG. 32 depicts a perspective view of a manifold assembly of the end effector of FIG. 32.

As best seen in FIG. 32, web (630) is formed by an upper half (632) and a lower half (634) that are joined together. Of course, such a configuration is merely optional. Web (630) defines a first internal passageway (640) and a second internal passageway (642). Passageway (640) is configured to align with and receive saline from irrigation lumen (616); while passageway (642) is configured to align with and receive saline from irrigation lumen (618). A plurality of additional passageways (644) branch off obliquely from passageway (640); while a plurality of additional passageways (646) branch off obliquely from passageway (642). Each passageway (646) terminates in a respective irrigation opening (636) formed in the lateral edge of web (630) near electrode (620). Each passageway (644) also terminates in a respective irrigation opening (not shown) formed in the lateral edge of web (630) near electrode (622). As saline is communicated distally through irrigation lumens (616, 618), the saline is expelled through irrigation openings (636) into gaps (G). As saline is expelled through irrigation openings (636), electrodes (620, 622) may be activated to apply RF electrosurgical energy to tissue that is in contact with electrodes (620, 622), while suction may be applied to the surgical site via one or more suction openings (not shown) of shaft (610). In some versions, passageways (640, 642, 644, 646) are formed as microfluidic channels, and capillary action will assist in transporting low pressure saline toward electrodes (620, 622).

Also in the present example, the positioning of irrigation openings (636) on sides that are lateral to electrodes (620, 622) may provide consistent functionality regardless of the angular orientation of end effector (600) about the longitudinal axis of shaft (610). In other words, end effector (600) may work just as well regardless of whether end effector (600) is flipped upside-down or right-side-up.

Figure 33:
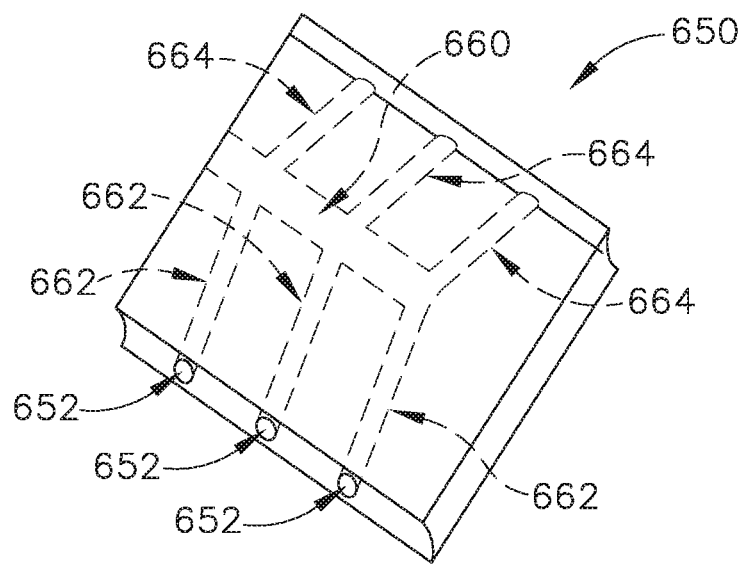
FIG. 33 depicts a perspective view of an exemplary alternative manifold assembly.

FIG. 33 shows an exemplary alternative web (650), which represents a variation of web (630) and may be positioned laterally between a pair of bipolar RF electrodes like the various electrodes described herein. Web (650) of this example comprises a single central passageway (660) that branches off obliquely into several additional passageways (662, 664). Passageways (662) branch off from one side of central passageway (660) while passageways (664) branch off from the other side of central passageway (660). Each passageway (662) terminates in a respective irrigation opening (652) formed in one lateral edge of web (650). Each passageway (664) also terminates in a respective irrigation opening (not shown) formed in the other lateral edge of web (650). As with web (630), saline may be communicated to passageway (660), with the saline ultimately being expelled via irrigation openings (652) to regions adjacent to RF electrodes.

Figure 34:
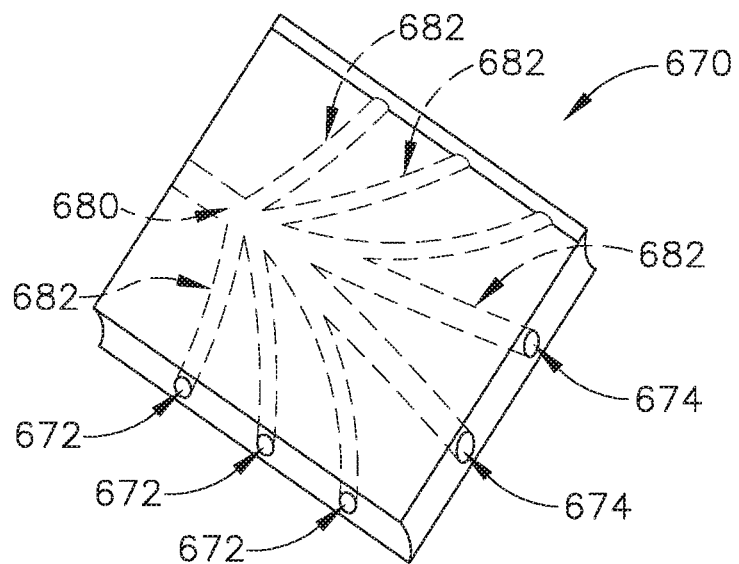
FIG. 34 depicts a perspective view of another exemplary perspective manifold assembly.

FIG. 34 shows another exemplary alternative web (670), which represents another variation of web (630) and may be positioned laterally between a pair of bipolar RF electrodes like the various electrodes described herein. Web (670) of this example comprises a single central passageway (680) that branches off into several additional passageways (682). Passageways (682) branch off from both lateral sides of central passageway (680); and distally from passageway (680). Laterally extending passageways (682) terminate in respective lateral irrigation openings (672) formed in lateral edges of web (670). Distally extending passageways (682) terminate in respective distal irrigation openings (674) formed in the distal edge of web (670). As with web (630), saline may be communicated to passageway (680), with the saline ultimately being expelled via irrigation openings (672, 674) to regions adjacent to RF electrodes and distal to RF electrodes.

In some variations, webs (330, 430, 530, 630, 650, 670) are provided as modular components of a kit, such that the operator may select the most appropriate web (330, 430, 530, 630, 650, 670) for the particular task at hand. Webs (330, 430, 530, 630, 650, 670) may also provide different rates of saline flow and/or other saline flow characteristics. Such differences in saline delivery may affect the operator's decision which web (330, 430, 530, 630, 650, 670) to choose for a particular procedure. In versions where webs (330, 430, 530, 630, 650, 670) are modular, such webs (330, 430, 530, 630, 650, 670) may be selectively coupled with a shaft (310, 410, 510, 610) via press fitting, snap fitting, or using any other suitable features or techniques as will be apparent to those of ordinary skill in the art in view of the teachings herein.

Figure 35:
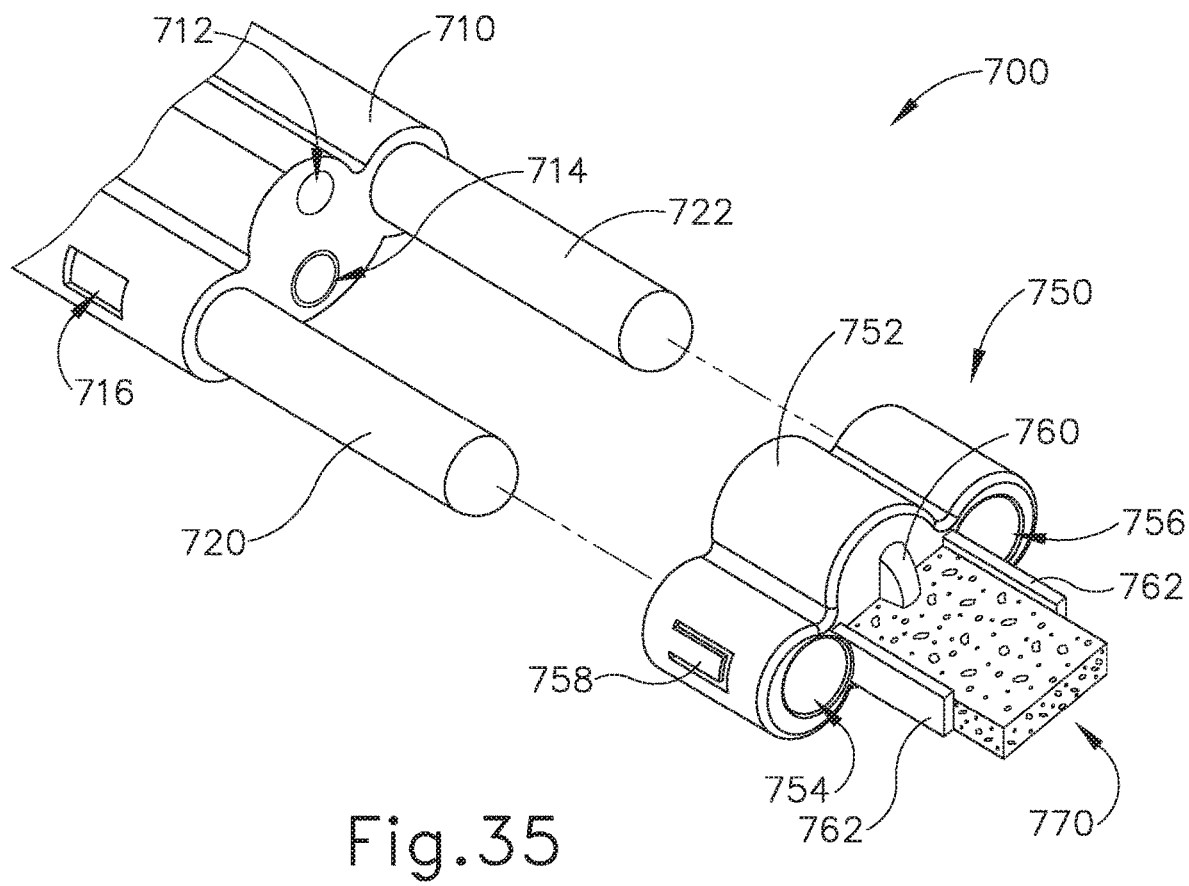
FIG. 35 depicts a perspective view of another exemplary alternative end effector, with a modular cap separated from the end effector.
Figure 36:
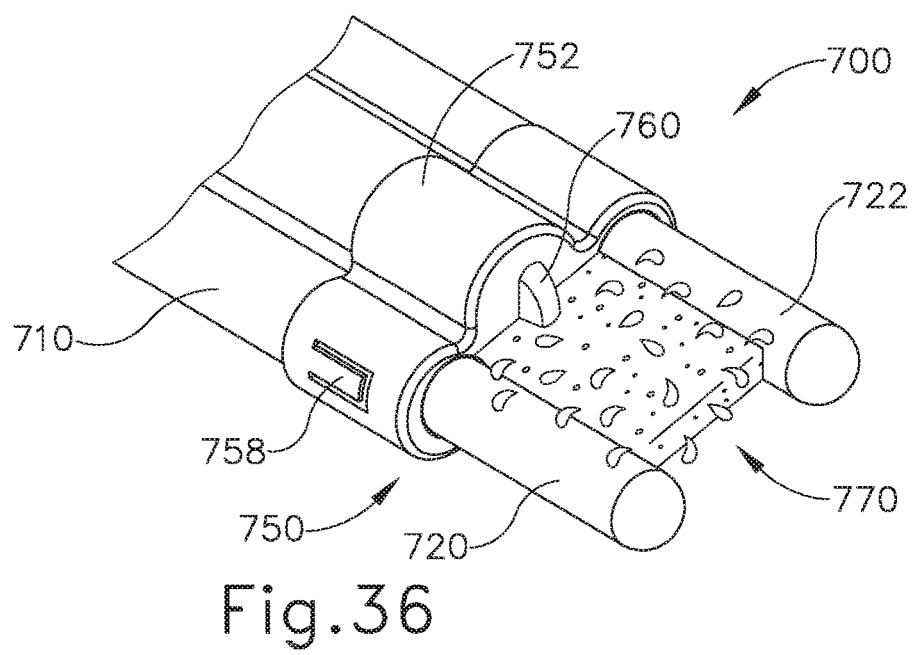
FIG. 36 depicts a perspective view of the modular cap of FIG. 35 secured to the end effector of FIG. 35.

FIGS. 35-36 show an exemplary alternative end effector (700) that is operable to removably couple with a modular irrigation cartridge (750). End effector (700) of this example comprises a pair of electrodes (720, 722) at the distal end of a shaft (710). Shaft (710) includes an irrigation lumen (712), a suction lumen (714), and a pair of snap-fit recesses (716). Cartridge (750) comprises a body (752) defining a pair of openings (754, 756) and a pair of snap arms (758). Openings (754, 756) are configured to receive respective electrodes (720, 722). Snap arms (758) comprise resilient cantilever arms with latching features that are configured to engage snap-fit recesses (716) to provide a snap-fit engagement between cartridge (750) and shaft (710). Cartridge (750) also includes a pair of distally extending arms (762), a fluid port (760), and a sponge member (770). Distally extending arms (762) are configured to be positioned adjacent to electrodes (720, 722) when cartridge (750) is secured to shaft (710). Arms (762) support and contain sponge member (770), thereby securing sponge member (770) in the region between electrodes (720, 722). While sponge member (770) comprises a sponge in the present example, any other suitable kind of porous member may be used.

Fluid port (760) is configured to fluidly couple with irrigation lumen (712) when cartridge (750) is secured to shaft (710). Fluid port (760) is further configured to redirect saline from irrigation lumen (712) to sponge member (770). Sponge member (770) absorbs saline until sponge member (770) becomes fully saturated. After reaching full saturation, additional saline is expressed by sponge member (770) onto electrodes (720, 722) and tissue adjacent to electrodes (720, 722). As the saline is so expressed, electrodes (720, 722) may be activated to apply RF electrosurgical energy to tissue that is in contact with electrodes (720, 722), while suction may be applied to the surgical site via the distal opening of suction lumen (714). By using sponge member (770) to provide dispersion of saline, the operability of end effector (700) and cartridge (750) may be relatively unaffected by the orientation of end effector (700). In other words, end effector (700) and cartridge (750) may work just as well regardless of whether end effector (700) and cartridge (750) are flipped upside-down or right-side-up.

In some surgical procedures, sponge member (770) may eventually deteriorate or otherwise become worn out, become clogged, or otherwise become inoperable. In such instances, the operator may simply remove cartridge (750) from end effector (700) and replace the spent cartridge (750) with a new cartridge (750). In some variations, the operator is presented with a selection of various kinds of cartridges having different features and functionalities, such that the operator may select the most appropriate cartridge for the task at hand and secure the selected cartridge to end effector (700). Various suitable alternative forms that such cartridges may take will be apparent to those of ordinary skill in the art in view of the teachings herein.

IV. Exemplary Combinations

The following examples relate to various non-exhaustive ways in which the teachings herein may be combined or applied. It should be understood that the following examples are not intended to restrict the coverage of any claims that may be presented at any time in this application or in subsequent filings of this application. No disclaimer is intended. The following examples are being provided for nothing more than merely illustrative purposes. It is contemplated that the various teachings herein may be arranged and applied in numerous other ways. It is also contemplated that some variations may omit certain features referred to in the below examples. Therefore, none of the aspects or features referred to below should be deemed critical unless otherwise explicitly indicated as such at a later date by the inventors or by a successor in interest to the inventors. If any claims are presented in this application or in subsequent filings related to this application that include additional features beyond those referred to below, those additional features shall not be presumed to have been added for any reason relating to patentability.

Example 1

An apparatus, comprising: (a) a shaft assembly, wherein the shaft assembly comprises: (i) an outer sheath having a distal end, (ii) at least one irrigation conduit extending through the outer sheath, wherein the at least one irrigation conduit is configured to couple with a source of irrigation fluid, and (iii) at least one suction conduit extending through the outer sheath, wherein the at least one suction conduit is configured to couple with a source of suction; and (b) an end effector, wherein the end effector comprises: (i) a first electrode extending distally relative to the distal end of the outer sheath, (ii) a second electrode extending distally relative to the distal end of the outer sheath, wherein the first and second electrodes are operable to apply bipolar RF energy to tissue, and (iii) a web extending laterally between the first and second electrodes, wherein the web is positioned distal to the distal end of the outer sheath.

Example 2

The apparatus of Example 1, wherein the web is in fluid communication with the at least one irrigation conduit.

Example 3

The apparatus of Example 2, wherein the web comprises a plurality of openings, wherein the openings are configured to expel fluid delivered to the web from the at least one irrigation conduit.

Example 4

The apparatus of Example 3, wherein the web has a top surface, a bottom surface, a distal edge, and a pair of lateral edges, wherein the lateral edges face the first and second electrodes, wherein at least some of the openings are formed through at least the top surface.

Example 5

The apparatus of Example 4, wherein at least some of the openings are rectangular.

Example 6

The apparatus of any one or more of Examples 4 through 5, wherein at least some of the openings are elliptical.

Example 7

The apparatus of any one or more of Examples 3 through 6, wherein the web has a top surface, a bottom surface, a distal edge, and a pair of lateral edges, wherein the lateral edges face the first and second electrodes, wherein at least some of the openings are formed through the lateral edges.

Example 8

The apparatus of any one or more of Examples 3 through 7, wherein the web comprises a plurality of microfluidic channels providing pathways for fluid communication from the at least one irrigation conduit to the openings.

Example 9

The apparatus of any one or more of Examples 1 through 8, wherein the web is porous.

Example 10

The apparatus of Example 9, wherein the web comprises a sponge.

Example 11

The apparatus of any one or more of Examples 1 through 10, wherein the end effector further comprises a cartridge body, wherein the web is fixedly secured to the cartridge body, wherein the cartridge body is removably coupled with the shaft assembly.

Example 12

The apparatus of Example 11, wherein the cartridge body and the shaft assembly comprise complementary snap-fitting features, wherein the complementary snap-fitting features are configured to removably couple the cartridge body with the shaft assembly.

Example 13

The apparatus of any one or more of Examples 11 through 12, wherein the cartridge body further comprises a pair of arms, wherein the web is fixedly secured to the cartridge body via the arms.

Example 14

The apparatus of Example 13, wherein the arms are positioned to be laterally interposed between the web and the first and second electrodes.

Example 15

The apparatus of any one or more of Examples 11 through 14, wherein the cartridge body further comprises a port, wherein the port is configured to direct irrigation fluid from the at least one irrigation conduit to the web.

Example 16

An apparatus, comprising: (a) a shaft assembly, wherein the shaft assembly comprises an outer sheath having a distal end; and (b) an end effector located at the distal end of the outer sheath, wherein the end effector comprises: (i) a first electrode extending distally relative to the distal end of the outer sheath, wherein the first electrode defines a first lateral recess, (ii) a second electrode extending distally relative to the distal end of the outer sheath, wherein the second electrode defines a second lateral recess, wherein the first and second electrodes are operable to apply bipolar RF energy to tissue, (iii) a first irrigation tube positioned in the first lateral recess, wherein the first irrigation tube is configured to dispense irrigation fluid adjacent to the first electrode, and (iv) a second irrigation tube positioned in the first lateral recess, wherein the second irrigation tube is configured to dispense irrigation fluid adjacent to the second electrode.

Example 17

The apparatus of Example 16, wherein the outer sheath further comprises a proximal end, wherein the outer sheath defines a full length extending between the distal end and the proximal end, wherein the first and second irrigation tubes extend along the full length of the outer sheath.

Example 18

The apparatus of any one or more of Examples 16 through 17, wherein the shaft assembly further comprises a first electrode rod and a second electrode rod, wherein the first electrode is formed at a distal end of the first electrode rod, wherein the second electrode is formed at a distal end of the second electrode rod, wherein the first and second electrode rods extend through the outer sheath.

Example 19

The apparatus of any one or more of Examples 16 through 18, further comprising a proximal suction port located at a proximal end of the shaft assembly, wherein the proximal suction port is configured to couple with a source of suction, wherein the end effector further includes at least one distal suction port, wherein the shaft assembly is configured to communicate suction from the proximal suction port to the distal suction port.

Example 20

A method of operating an instrument, comprising: (a) positioning a pair of electrodes adjacent to tissue, wherein the electrodes are located at an end effector of the instrument; (b) applying suction via the end effector; and (c) dispensing an irrigation fluid to the electrodes and to the tissue, wherein the act of dispensing an irrigation fluid to the electrodes and to the tissue comprises communicating irrigation fluid along a shaft of the instrument to a web of the end effector, wherein the web is laterally interposed between the electrodes, wherein the web is positioned distal to the shaft, wherein the web disperses the irrigation fluid.

V. Miscellaneous

It should be understood that any one or more of the teachings, expressions, embodiments, examples, etc. described herein may be combined with any one or more of the other teachings, expressions, embodiments, examples, etc. that are described herein. The above-described teachings, expressions, embodiments, examples, etc. should therefore not be viewed in isolation relative to each other. Various suitable ways in which the teachings herein may be combined will be readily apparent to those of ordinary skill in the art in view of the teachings herein. Such modifications and variations are intended to be included within the scope of any claims.

It should be appreciated that any patent, publication, or other disclosure material, in whole or in part, that is said to be incorporated by reference herein is incorporated herein only to the extent that the incorporated material does not conflict with existing definitions, statements, or other disclosure material set forth in this disclosure. As such, and to the extent necessary, the disclosure as explicitly set forth herein supersedes any conflicting material incorporated herein by reference. Any material, or portion thereof, that is said to be incorporated by reference herein, but which conflicts with existing definitions, statements, or other disclosure material set forth herein will only be incorporated to the extent that no conflict arises between that incorporated material and the existing disclosure material.

Versions of the devices described above may have application in conventional medical treatments and procedures conducted by a medical professional, as well as application in robotic-assisted medical treatments and procedures. By way of example only, various teachings herein may be readily incorporated into a robotic surgical system such as the DAVINCI™ system by Intuitive Surgical, Inc., of Sunnyvale, Calif. Similarly, those of ordinary skill in the art will recognize that various teachings herein may be readily combined with various teachings of any of the following: U.S. Pat. No. 5,792,135, entitled "Articulated Surgical Instrument For Performing Minimally Invasive Surgery With Enhanced Dexterity and Sensitivity," issued Aug. 11, 1998, the disclosure of which is incorporated by reference herein; U.S. Pat. No. 5,817,084, entitled "Remote Center Positioning Device with Flexible Drive," issued Oct. 6, 1998, the disclosure of which is incorporated by reference herein; U.S. Pat. No. 5,878,193, entitled "Automated Endoscope System for Optimal Positioning," issued Mar. 2, 1999, the disclosure of which is incorporated by reference herein; U.S. Pat. No. 6,231,565, entitled "Robotic Arm DLUS for Performing Surgical Tasks," issued May 15, 2001, the disclosure of which is incorporated by reference herein; U.S. Pat. No. 6,783,524, entitled "Robotic Surgical Tool with Ultrasound Cauterizing and Cutting Instrument," issued Aug. 31, 2004, the disclosure of which is incorporated by reference herein; U.S. Pat. No. 6,364,888, entitled "Alignment of Master and Slave in a Minimally Invasive Surgical Apparatus," issued Apr. 2, 2002, the disclosure of which is incorporated by reference herein; U.S. Pat. No. 7,524,320, entitled "Mechanical Actuator Interface System for Robotic Surgical Tools," issued Apr. 28, 2009, the disclosure of which is incorporated by reference herein; U.S. Pat. No. 7,691,098, entitled "Platform Link Wrist Mechanism," issued Apr. 6, 2010, the disclosure of which is incorporated by reference herein; U.S. Pat. No. 7,806,891, entitled "Repositioning and Reorientation of Master/Slave Relationship in Minimally Invasive Telesurgery," issued Oct. 5, 2010, the disclosure of which is incorporated by reference herein; U.S. Pat. No. 8,844,789, entitled "Automated End Effector Component Reloading System for Use with a Robotic System," issued Sep. 30, 2014, the disclosure of which is incorporated by reference herein; U.S. Pat. No. 8,820,605, entitled "Robotically-Controlled Surgical Instruments," issued Sep. 2, 2014, the disclosure of which is incorporated by reference herein; U.S. Pat. No. 8,616,431, entitled "Shiftable Drive Interface for Robotically-Controlled Surgical Tool," issued Dec. 31, 2013, the disclosure of which is incorporated by reference herein; U.S. Pat. No. 8,573,461, entitled "Surgical Stapling Instruments with Cam-Driven Staple Deployment Arrangements," issued Nov. 5, 2013, the disclosure of which is incorporated by reference herein; U.S. Pat. No. 8,602,288, entitled "Robotically-Controlled Motorized Surgical End Effector System with Rotary Actuated Closure Systems Having Variable Actuation Speeds," issued Dec. 10, 2013, the disclosure of which is incorporated by reference herein; U.S. Pat. No. 9,301,759, entitled "Robotically-Controlled Surgical Instrument with Selectively Articulatable End Effector," issued Apr. 5, 2016, the disclosure of which is incorporated by reference herein; U.S. Pat. No. 8,783,541, entitled "Robotically-Controlled Surgical End Effector System," issued Jul. 22, 2014, the disclosure of which is incorporated by reference herein; U.S. Pat. No. 8,479,969, entitled "Drive Interface for Operably Coupling a Manipulatable Surgical Tool to a Robot," issued Jul. 9, 2013; U.S. Pat. No. 8,800,838, entitled "Robotically-Controlled Cable-Based Surgical End Effectors," issued Aug. 12, 2014, the disclosure of which is incorporated by reference herein; and/or U.S. Pat. No. 8,573,465, entitled "Robotically-Controlled Surgical End Effector System with Rotary Actuated Closure Systems," issued Nov. 5, 2013, the disclosure of which is incorporated by reference herein.

Versions of the devices described above may be designed to be disposed of after a single use, or they can be designed to be used multiple times. Versions may, in either or both cases, be reconditioned for reuse after at least one use. Reconditioning may include any combination of the steps of disassembly of the device, followed by cleaning or replacement of particular pieces, and subsequent reassembly. In particular, some versions of the device may be disassembled, and any number of the particular pieces or parts of the device may be selectively replaced or removed in any combination. Upon cleaning and/or replacement of particular parts, some versions of the device may be reassembled for subsequent use either at a reconditioning facility, or by a clinician immediately prior to a procedure. Those skilled in the art will appreciate that reconditioning of a device may utilize a variety of techniques for disassembly, cleaning/replacement, and reassembly. Use of such techniques, and the resulting reconditioned device, are all within the scope of the present application.

By way of example only, versions described herein may be sterilized before and/or after a procedure. In one sterilization technique, the device is placed in a closed and sealed container, such as a plastic or TYVEK bag. The container and device may then be placed in a field of radiation that can penetrate the container, such as gamma radiation, x-rays, or high-energy electrons. The radiation may kill bacteria on the device and in the container. The sterilized device may then be stored in the sterile container for later use. A device may also be sterilized using any other technique known in the art, including but not limited to beta or gamma radiation, ethylene oxide, or steam.

Having shown and described various embodiments of the present invention, further adaptations of the methods and systems described herein may be accomplished by appropriate modifications by one of ordinary skill in the art without departing from the scope of the present invention. Several of such potential modifications have been mentioned, and others will be apparent to those skilled in the art. For instance, the examples, embodiments, geometrics, materials, dimensions, ratios, steps, and the like discussed above are illustrative and are not required. Accordingly, the scope of the present invention is understood not to be limited to the details of structure and operation shown and described in the specification and drawings.

We claim:

1. An apparatus, comprising:
   (a) a shaft assembly, wherein the shaft assembly comprises:
      (i) an outer sheath having a distal end, and
      (ii) at least one irrigation conduit extending through the outer sheath, wherein the at least one irrigation conduit is configured to couple with a source of an irrigation fluid;
   (b) an end effector, wherein the end effector comprises:
      (i) a first electrode extending distally relative to the distal end of the outer sheath,
      (ii) a second electrode extending distally relative to the distal end of the outer sheath, wherein the first and second electrodes are operable to apply bipolar RF energy to tissue, and
      (iii) a web extending laterally between the first and second electrodes, wherein the web is positioned distal to the distal end of the outer sheath, wherein the web is removably coupled with the end effector, wherein when the web is attached it is fluidly coupled with the at least one irrigation conduit and configured to receive the irrigation fluid therefrom, wherein the web is operable to express the irrigation fluid, wherein when the web is detached it is fluidly uncoupled from the at least one irrigation conduit.

2. The apparatus of claim 1, wherein when the web is attached it is selectively operable to discharge the irrigation fluid.

3. The apparatus of claim 1, wherein the web is porous.

4. The apparatus of claim 3, wherein the web comprises a sponge.

5. The apparatus of claim 1, wherein the end effector further comprises a cartridge body, wherein the web is fixedly secured to the cartridge body, wherein the cartridge body is removably coupled with the shaft assembly.

6. The apparatus of claim 5, wherein the cartridge body and the shaft assembly comprise complementary snap-fitting features, wherein the complementary snap-fitting features are configured to removably couple the cartridge body with the shaft assembly.

7. The apparatus of claim 5, wherein the cartridge body further comprises a pair of arms, wherein the web is fixedly secured to the cartridge body via the arms.

8. The apparatus of claim 7, wherein the arms are positioned to be laterally interposed between the web and the first and second electrodes to separate the web from the first and second electrodes.

9. The apparatus of claim 5, wherein the cartridge body further comprises a port, wherein the port is configured to direct irrigation fluid from the at least one irrigation conduit to the web.

10. The apparatus of claim 1, wherein the shaft assembly further comprises at least one suction conduit extending through the outer sheath, wherein the at least one suction conduit is configured to couple with a source of suction.

11. An apparatus, comprising:
(a) a shaft assembly, wherein the shaft assembly comprises:
  (i) an outer sheath having a distal end,
  (ii) at least one irrigation conduit extending through the outer sheath, wherein the at least one irrigation conduit is configured to couple with a source of an irrigation fluid, and
  (iii) at least one suction conduit extending through the outer sheath, wherein the at least one suction conduit is configured to couple with a source of suction; and
(b) an end effector, wherein the end effector comprises:
  (i) a first electrode extending distally relative to the distal end of the outer sheath,
  (ii) a second electrode extending distally relative to the distal end of the outer sheath, wherein the first and second electrodes are operable to apply bipolar RF energy to tissue,
  (iii) a web extending laterally between the first and second electrodes, wherein the web is positioned distal to the distal end of the outer sheath, wherein the web is fluidly coupled with the at least one irrigation conduit and configured to receive the irrigation fluid therefrom, wherein the web is selectively operable to discharge the irrigation fluid from the irrigation conduit through a surface of the web, and
  (iv) a cartridge body, wherein the web is fixedly secured to the cartridge body, wherein the cartridge body is removably coupled with the shaft assembly.

12. The apparatus of claim 11, wherein the cartridge body and the shaft assembly comprise complementary snap-fitting features, wherein the complementary snap-fitting features are configured to removably couple the cartridge body with the shaft assembly.

13. The apparatus of claim 11, wherein the cartridge body further comprises a pair of arms, wherein the web is fixedly secured to the cartridge body via the arms.

14. The apparatus of claim 13, wherein the arms are positioned to be laterally interposed between the web and the first and second electrodes.

15. The apparatus of claim 11, wherein the cartridge body further comprises a port, wherein the port is configured to direct irrigation fluid from the at least one irrigation conduit to the web.

* * * * *